(12) United States Patent
Goodwin, Jr.

(10) Patent No.: US 8,129,175 B2
(45) Date of Patent: Mar. 6, 2012

(54) POINT SOURCE DIFFUSION CELL ACTIVITY ASSAY APPARATUS

(75) Inventor: Richard H. Goodwin, Jr., Bethesda, MD (US)

(73) Assignee: Neuro Probe Incorporated, Gaithersburg, MD (US)

( * ) Notice: Subject to any disclaimer, the term of this patent is extended or adjusted under 35 U.S.C. 154(b) by 191 days.

(21) Appl. No.: 12/483,012

(22) Filed: Jun. 11, 2009

(65) Prior Publication Data

US 2009/0246860 A1 Oct. 1, 2009

Related U.S. Application Data

(63) Continuation of application No. 11/201,302, filed on Aug. 11, 2005, now Pat. No. 7,547,525.

(60) Provisional application No. 60/600,783, filed on Aug. 12, 2004.

(51) Int. Cl.
  *C12M 1/34* (2006.01)
  *C12M 3/00* (2006.01)

(52) U.S. Cl. .................. 435/287.2; 435/287.9; 422/559

(58) Field of Classification Search ............... 435/287.1, 435/287.9; 422/502, 511, 551, 552, 559
See application file for complete search history.

(56) References Cited

U.S. PATENT DOCUMENTS

| | | | |
|---|---|---|---|
| 4,912,057 A | 3/1990 | Guirguis et al. | |
| 5,200,152 A * | 4/1993 | Brown | 422/503 |
| 5,210,021 A | 5/1993 | Goodwin, Jr. | |
| 5,284,753 A | 2/1994 | Goodwin, Jr. | |
| 5,302,515 A | 4/1994 | Goodwin, Jr. | |
| 5,514,555 A | 5/1996 | Springer et al. | |
| 5,601,997 A | 2/1997 | Tchao | |
| 5,716,849 A | 2/1998 | Ligon et al. | |
| 5,888,807 A | 3/1999 | Palsson et al. | |
| 5,906,940 A | 5/1999 | Wandrey et al. | |
| 6,287,340 B1 | 9/2001 | Altman et al. | |
| 6,329,164 B1 | 12/2001 | Goodwin, Jr. | |
| 6,395,505 B2 | 5/2002 | Goodwin, Jr. | |
| 6,468,786 B2 | 10/2002 | Goodwin, Jr. | |
| 6,576,433 B1 | 6/2003 | Keller et al. | |
| 6,767,401 B2 | 7/2004 | Goodwin, Jr. | |
| 6,833,269 B2 | 12/2004 | Carpenter | |

(Continued)

FOREIGN PATENT DOCUMENTS

AU 2005272814 4/2011

(Continued)

OTHER PUBLICATIONS

European Search Report, Nov. 7, 2007.

(Continued)

*Primary Examiner* — William H Beisner
*Assistant Examiner* — Michael Hobbs
(74) *Attorney, Agent, or Firm* — Plumsea Law Group, LLC

(57) ABSTRACT

Apparatuses and methods for determining whether a test compound solution induces cell activity, an embodiment of the method of the present invention comprising placing a test compound solution in contact with a cell suspension media containing cells, diffusing the test compound solution into the cell suspension from a point source, and detecting activity in the cells with respect to their distance from the point source. Detecting activity in the cells can involve detecting activity in a first group of the cells proximate to the point source, and detecting activity in a second group of the cells farther from the point source than the first group.

25 Claims, 13 Drawing Sheets

U.S. PATENT DOCUMENTS

| | | | |
|---|---|---|---|
| 7,014,706 | B2 | 3/2006 | Goodwin, Jr. |
| 7,332,029 | B2 | 2/2008 | Goodwin, Jr. |
| 7,704,325 | B2 | 4/2010 | Goodwin, Jr. |
| 2002/0146680 | A1 | 10/2002 | Rich |
| 2002/0150503 | A1* | 10/2002 | Tanaka et al. .................. 422/58 |
| 2003/0022363 | A1 | 1/2003 | Rao et al. |
| 2004/0014205 | A1 | 1/2004 | Banes |
| 2004/0071599 | A1 | 4/2004 | Rusch et al. |
| 2004/0126876 | A1 | 7/2004 | Ravin et al. |

FOREIGN PATENT DOCUMENTS

| | | |
|---|---|---|
| EP | 1786921 | 1/2011 |
| JP | 08505530 | 6/1996 |
| WO | 9416098 | 7/1994 |
| WO | WO 00/55298 | 9/2000 |
| WO | WO 2006/020766 | 2/2006 |

OTHER PUBLICATIONS

European Office Action, Sep. 2, 2008.
PCT/US05/28546—International Search Report and Written Opinion.
Journal of Immunological Methods "Rapid flourescence-based measurement of neutrophil migration in vitro"; C.W. Frevert, V.A. Wong, R.B. Goodman, R. Goodwin and T. R. Martin; Aug. 1997.
Journal of Immunological Methods "Improved rapid photometric assay for quantitative measurement of PMN migration"; W.G. Junger, T.A. Cardoza, F.C. Liu, D.B. Hoyt and R. Goodwin; Aug. 1992.
"Spatial Control of Actin Polymerization During Neutrophil Chemataxis" by Orin D. Weiner, Guy Servant, Matthew D. Welch, Timothy J. Mitchison, John W. Sedat and Henry R. Bourne; Nature Cell Biology—vol. 1—Jun. 1999; http://www.cellbio.nature.com.
Robert D. Nelson, et al., "Chemotaxis under Agarose: A New and Simple method for Measuring Chemotaxis and Spontaneous Migration of human Polymorphonuclear Leukocytes and Monocytes", J. Immunology 1975, pp. 1650-1656, vol. 115(6), The Williams & Wilkins Co.
European Office Action dated Mar. 27, 2009.
"Dictyostellum Chemotactic Response to Spatial and Temporal Gradients. Theories of the Limits of Chemotactic Sensitivity and of Pseudochemotaxis" by R.P. Futrelle; Biology and Computing Research Group, Department of Genetics and Development; University of Illinois, Urbana, Illinois 61801; Journal of Cellular Biochemistry 18:197-212 (1982), Cellular Recognition 603-618.
"Store-operated calcium channel regulates chemotactic behavior of ascidian sperm" by Manabu Yoshida, Makiko Ishikawa, Hiroko izumi, Rosaria De Santis and Masaaki Morisawa; Misaki Marine Biological Station, Graduate School of Science, University of Tokyo, Miura, Kanagawa 238-0225, Japan; and Laboratory of Cell Biology, Stazione Zoologica Anton Dohrn, Villa Comunale, 80121 Naples, Italy; www.pnas.org/cgi/doi/10.1073/pnas.0135565100; PNAS, Jan. 7, 2003, vol. 100, No. 1, 149-154.
Japanese Office Action dated May 10, 2011 in Japanese Application No. 2007525788. English translation submitted hereto.
Response to Japanese Office Action filed Aug. 26, 2011 in Japanese Application No. 2007525788. English translation submitted hereto.
European Office Action dated Feb. 15, 2008 in European Application No. 05785092.7.
Response to European Office Action filed Jul. 31, 2008 in European Application No. 05785092.7.
European Office Action dated Sep. 2, 2008 in European Application No. 05785092.7.
Response to European Office Action filed Mar. 12, 2009 in European Application No. 05785092.7.
European Office Action dated Mar. 27, 2009 in European Application No. 05785092.7.
Response to European Office Action filed Sep. 11, 2009 in European Application No. 05785092.7.
European Office Action dated Sep. 23, 2009 in European Application No. 05785092.7.
Response to European Office Action filed Jan. 29, 2010 in European Application No. 05785092.7.
European Office Action dated Apr. 16, 2010 in European Application No. 05785092.7.
Response to European Office Action filed Jun. 4, 2010 in European Application No. 05785092.7.
Notice of Allowance dated Jul. 26, 2010 in European Application No. 05785092.7.
Decision to Grant a European Patent dated Dec. 16, 2010 in European Application No. 05785092.7.
Australian Office Action dated Sep. 6, 2010 in Australian Application No. 2005272814.
Response to Australian Office Action filed Dec. 2, 2010 in Australian Application No. 2005272814.
Notice of Acceptance dated Dec. 14, 2010 in Australian Application No. 2005272814.

* cited by examiner

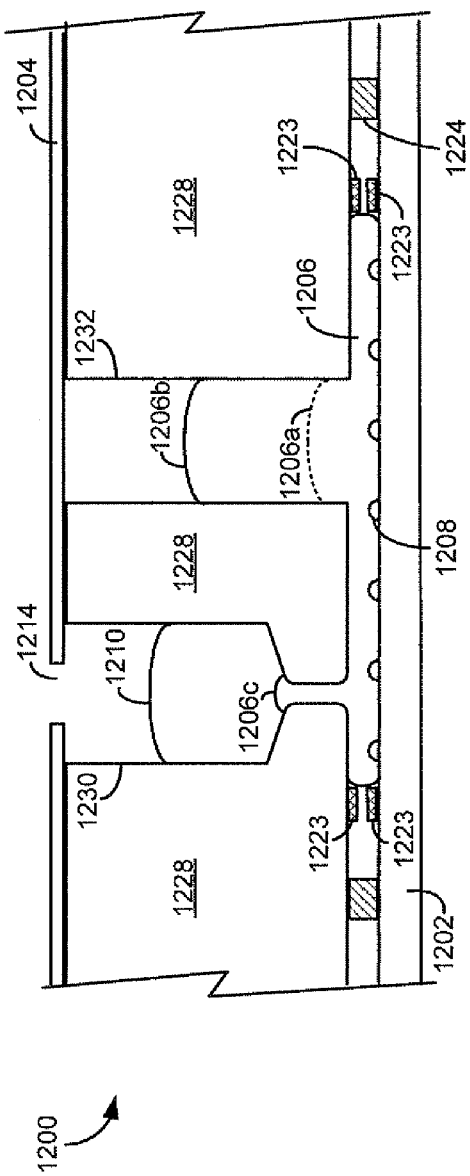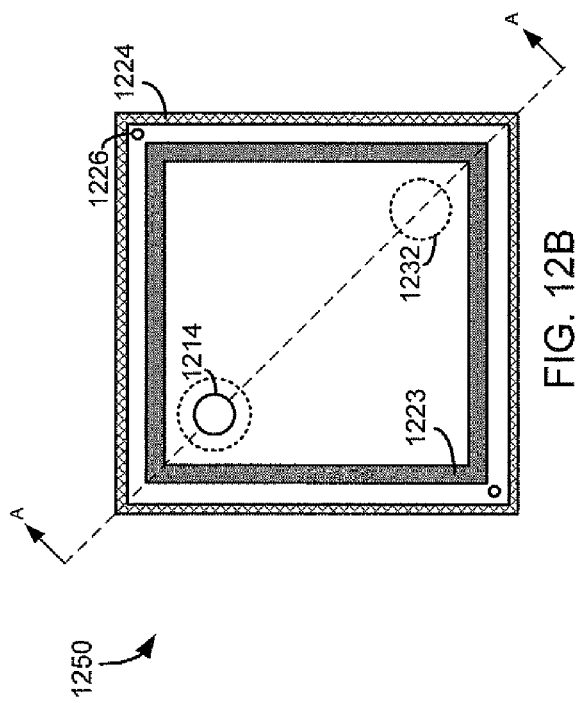
FIG. 12A
FIG. 12B

POINT SOURCE DIFFUSION CELL ACTIVITY ASSAY APPARATUS

This is a continuation of U.S. patent application Ser. No. 11/201,302, filed Aug. 11, 2005, now U.S. Pat. No. 7,547,525, which claims the benefit of U.S. Provisional Application No. 60/600,783, filed Aug. 12, 2004, both of which are herein incorporated by reference in their entirety.

BACKGROUND

1. Field of the Invention

The present invention relates to methods and apparatus for high content screening (HCS) and high throughput screening (HTS). In particular, the present invention relates to cell activity assays (CAA) involving chemotaxis, migration, angiogenesis, growth, proliferation, and other cell activity based on, for example, morphology, shape, and movement of cells. The present invention also relates to cell activity assays involving changes internal to cells such as differentiation, alteration of metabolic rate, and movement of molecules within a cell initiated by activation of receptors in the cell membrane. The present invention also relates to cell activity assays involving the interaction of cells in response to various chemical environments, and the interaction of different cell types with one another. The present invention also relates to assays involving the penetration of cell layers by chemical compounds or other entities, and to assays for ascertaining the diffusion rate of members of a compound library through various confluent cell layers, e.g., endothelial or epithelial cell layers.

2. Background of the Invention

Pharmaceutical companies expend considerable resources on researching and developing drug therapies. The research and development process, from conception to eventual approval by the Food and Drug Administration (FDA), can last several years. Thus, in the initial stages, it is highly desirable to quickly rule out unusable chemical substances and focus efforts on effective substances.

In developing drug therapies, pharmaceutical companies typically start with a vast library of chemicals. From this library, a large number of the chemicals may have the potential to therapeutically act on the cells associated with the disease or ailment for which the drug is being developed. Determining which chemicals affect the cells is therefore an important step in drug development.

Chemotaxis is the directional movement (migration) of biological cells or organisms in response to concentration gradients of chemicals. Invasion is the movement (migration) of cells into or through a barrier. Tumor invasion is such action initiated by cancer cells into or through biological tissue in vivo, or, into or through extra cellular matrix proteins, e.g., collagen or matrigel, into or through barriers made of other substances, in vitro. Angiogenesis is the migration and formation of capillary blood vessels by endothelial cells. Growth is the increase in the size, form, or complexity of cells. Proliferation is growth of cells by cell division. Differentiation is the process by which cells change from a less specialized to a more specialized state usually associated with different functional roles and the expression of new and different traits. Interaction of cells is the alteration of cell behavior such as movement, invasion, angiogenesis, growth, proliferation, or differentiation in response to the presence and action of nearby cells of the same or different type.

The movement of compounds and structures within cells is another kind of cell activity that can be of interest in drug discovery. For example, powerful new optical detection systems can track the movement of florescent compounds (e.g., proteins) within the cell. Many different changes in internal cell activities in response to contact by compounds from a library with the cell's membrane and/or receptors can be observed with these new detection systems. These activities and similar activities are referred to herein collectively as "cell activity," and the apparatus employed to perform the assays are referred to herein as "cell activity assay apparatus."

One kind of single-site conventional cell activity assay apparatus referred to variously in the literature as "chemotaxis chambers," "Boyden chambers," "Boyden chemotaxis chambers," "blind well chambers," or "microchemotaxis chambers," comprises two compartments separated by a membrane, with one or both of the compartments open to air. Multi-site apparatus are referred to as "multi-well chemotaxis chambers," or "multi-well Boyden chambers," and have the same basic site structure but have multiple sites. (See, e.g., U.S. Pat. Nos. 5,210,021 and 5,302,515.)

Assays employing this kind of apparatus pipette cells suspended in media into the upper compartments, and pipette chemotactic factors and controls into the bottom compartments. The chemotactic factors can be used in various dilutions to get a dose-response curve. The controls are generally of three kinds: (a) negative, when the same media that is used to suspend the cells is also used below the membrane, (b) chemokinetic, when a chemotactic factor is placed at the same concentration in the media with the cells and in the well on the opposite side of the membrane, and (c) positive, when a known chemoattractant is placed in the bottom wells. Chemokinetic controls allow the user to distinguish heightened random activity of the cells, due to contact with the chemotactic factor, from directional response in a concentration gradient of that chemotactic factor.

Cell activity assay apparatus can also be used to measure the response of cells of different origins—e.g., immune cells obtained from patients suffering from diseases—to a chemotactic factor of known chemotactic activity. In this case, the cells in question are interrogated by both a negative control and a known chemotactic factor to see if the differential response is depressed or normal.

Traditionally, chemotactic activity has been measured by establishing a stable concentration gradient in the cell activity assay apparatus; incubating it for a predetermined time; and then counting the cells that have migrated through the membrane (or into the membrane). A comparison is then made between the activity of the cells in a concentration gradient of the chemotactic factor being tested, and the activity of the cells in the absence of the concentration gradient.

In one type of conventional cell activity assay apparatus and method, the chemotactic response is measured by physically counting the number of cells on the membrane surface closest to the chamber containing the chemical agent. An example of this type of cell activity assay apparatus is described in U.S. Pat. No. 5,210,021 (Goodwin, Jr.), which is hereby incorporated by reference. One prior art method of obtaining quantitative data is to remove the membrane from the cell activity assay apparatus, remove the cells from the membrane surface closest to the chamber containing the original cell suspension, fix and stain the remaining cells, and then observe and count the stained cells under a microscope. Because of the time and expense associated with examining the entire membrane, only representative areas of the membrane are counted, rendering results less accurate than would otherwise be the case if the entire membrane were examined and counted.

Cell activity assays using a disposable ninety-six well microplate format, for example the ChemoTx™ System (available from Neuro Probe, Inc., Gaithersburg, Md.), are amenable to different methods of quantification of results. The manual staining and counting method described above can be used, but is not recommended due to the time involved. A preferred method is to centrifuge the microplate with the filter attached such that the cells that have migrated through the filter are deposited onto the bottom of the lower wells. The cells are then stained with MTT, MTS (available from Promega, Madison, Wis.), or a similar dye, and then read in a standard automated laboratory densitometric reader (sometimes referred to as an Elisa plate reader).

Another method of obtaining quantitative data with this apparatus is to dye the cells with a fluorescent material, e.g., Calcein AM (available from Molecular Probes, Eugene, Ore.); centrifuge the migrated cells into the microplate; and count cells with an automatic fluorescence plate reader (e.g., Cytofluor available from PE Biosystems, Foster City, Calif., Victor$^2$ available from EG&G Wallac, Gaithersburg, Md., or fmax available from Molecular Devices, Sunnyvale, Calif.). The automatic plate reader excites the fluorescent dye in the migrated cells with one wavelength of light and reads the light emitted at a second wavelength. Alternatively, the cells that have not migrated are removed from the top of each site, and the plate with the framed membrane attached is read in the automatic fluorescent plate reader without spinning the cells into the plate, thereby counting the cells that have fallen off the filter into the lower well as well as those on the bottom of the membrane and in the pores of the membrane.

As described above, the past efforts at measuring chemotactic activity have focused on measuring or counting cells that have passed through a long, tortuous path, such as through a filter or thick membrane. Because of their dependence on cell migration, these techniques suffer from at least three significant drawbacks. First, the cells must migrate a considerable distance through the media to the chemotactic factor, which can add substantial time to the assay. Second, to obtain desirable (low) coefficients of variation, a relatively large number of cells is needed to calculate percentages of migration. Consequently, these assays demand large volumes of compound from a compound library, which are not always readily available. Third, in migration assays that count the number or percentage of cells that have passed through a filter, the results provide quantitative data, but not kinetic data. In addition, the results provide no information about the cells that have not passed through the filter.

ABBREVIATIONS & DEFINITIONS

1. "High throughput screening" is herein abbreviated to "HTS."
2. "Cell-based high throughput screening" is herein abbreviated to "CBHTS."
3. "High Content Screening" is herein abbreviated to "HCS."
4. "Nanometer" is herein abbreviated to "nm."
5. "Microliters" is herein abbreviated to "µl."
6. "Micrograms" is herein abbreviated to "µg."
7. "Cell activity assay apparatus" is herein abbreviated to "CAAA."
8. "Test compound solution" is herein abbreviated to "TCS" and refers to a solution composed of a compound from a compound library dissolved in water, cell culture media, dimethyl sulfoxide (DMSO), other appropriate media, or a combination thereof.
9. "Cell suspension media" is herein abbreviated to "CSM" and refers to a media or fluid capable of suspending cells.
10. "Cell suspension" is herein abbreviated to "CS" and refers to a solution containing cells suspended in a cell suspension media.
11. "Point source" is herein abbreviated to "PS" and refers to a center area from which a chemical compound diffuses concentrically.

SUMMARY OF THE INVENTION

The present invention provides apparatus and methods for rapidly and accurately assessing whether and to what extent cell activity is affected by compounds that make contact with a cell membrane. The present invention performs this assessment with minimal cost in cells, reagents, assay platforms, and other disposables, and with very low coefficients of variability, thus allowing primary screening of large compound libraries without using duplicate or triplicate sites for each compound.

The present invention provides an assay apparatus for HCS, HTS, CBHTS, and cell based screening, as well as basic research in cell activity. The apparatus and method of the present invention facilitate cell activity assays. In particular, the present invention provides means for assessing whether compounds from a compound library can induce cell activity, e.g., chemotaxis. In contrast to the prior art, the present invention allows for the determination of cell activity by detecting changes in cells that occur well before a cell could migrate through a membrane. These changes include, for example, cell orientation, internal morphological changes, temperature variations, molecular movement within the cell, and electromagnetic changes—in short, any change in cells that can be detected.

The present invention provides a point source from which a test compound solution diffuses into a cell suspension media and contacts cells. The term "point" as used herein in the expression "point source" is not a geometric term, but a relative term referring to a center area from which a compound diffuses concentrically. Since the area of a point source in this usage is relatively small with respect to the area of the entire site (e.g., approximately 10% of area of the entire site), diffusion from the center area into the rest of the site is experimentally equivalent to diffusion from a point. As an example, the concentric diffusion can be readily observed from a top view of a site, with progressive rings extending outward from the point source in circles or in portions of circles (e.g., semicircles or quarter circles) depending on the configuration of the site and the location of the point source.

The present invention controls the rate of this diffusion so that cell activity can be progressively monitored. In one aspect of the present invention, the rate of diffusion is gradual so that the cell activity caused by the test compound solution occurs in stages as the test compound solution diffuses farther from the point source, and so that periodic readings of the site can detect such progressive changes. Embodiments of the present invention control the rate of diffusion using, for example, an opening through a film, a gel occluding an opening through a film, a gel containing test compound solution, a sintered material containing test compound solution, a frozen test compound solution, a dried or freeze-dried test compound solution, and combinations thereof.

One embodiment of the present invention provides a method for determining whether a test compound solution induces cell activity comprising placing the test compound solution in contact with a cell suspension media containing cells, diffusing the test compound solution into the cell suspension media from a point source, and detecting activity in the cells with respect to their distance from the point source.

Detecting activity in the cells can involve detecting activity in a first group of the cells proximate to the point source, and detecting activity in a second group of the cells farther from the point source than the first group.

Another embodiment of the present invention provides a cell activity assay apparatus that includes a film having two sides, an opening through the film, cell suspension media disposed on a first side of the film over the opening, cells settled on the first side of the film, and test compound solution disposed on a second side of the film over the opening. In this configuration, the test compound solution contacts the cell suspension media within or proximate to the opening, and diffuses into the cell suspension media, creating a concentration gradient emanating from the opening into the cell suspension media on the first side of the film. In one embodiment, the opening is a hole and the concentration gradient extends concentrically from the opening. As such, the cells nearest the opening are contacted first by the test compound solution. Subsequently, as the test compound solution diffuses farther from the opening, the other cells are contacted radially outward in stages. If the cells are responsive to the test compound solution, the progressive diffusion provides progressive cell activity that, when monitored with suitable detection means, yields both quantitative and kinetic (e.g., changes in the cells as a function of time) data on cell activity.

An embodiment of the present invention provides a method for performing a cell activity assay using the apparatus described above. According to this method, a cell suspension is deposited onto the first side of a film over the opening. The film is then incubated, which allows cells to settle out of the cell suspension and adhere to the first side of the film, leaving cells adhered to the first side and cell suspension media covering the cells. Optionally, the film is then read to provide a baseline reading of the cells. The test compound solution is then deposited on the second side of the film over the opening. The test compound solution can be deposited, for example, by inverting the film and pipetting onto the second side of the film, by inverting a pin applicator and applying the test compound solution up onto the second side of the film, by projecting the test compound solution upward, or by other appropriate means. Preferably, in depositing the cell suspension and the test compound solution, the solutions are centered over the opening.

With the test compound solution deposited on the second side of the film, the test compound solution is in contact with the cell suspension media at the opening in the film. With this contact, the test compound solution begins diffusing into the cell suspension media. The site is then read periodically to observe the effect of the test compound solution on the cells as this diffusion progresses. These readings detect, for example, cell elongation and orientation, other morphological changes, temperature changes, movement of molecules and structures within a cell, and electromagnetic changes. Detecting morphological changes involves, for example, examining the aspect ratio (length to width ratio) of the cells. Detecting cell orientation involves, for example, examining the orientation of the aspect ratio in relation to the opening from which the test compound solution is diffusing.

Alternatively, the apparatus described above can also be used first in assay development to determine the optimal time to perform a single detection step, and then in the screening stage (which is typically the expensive time and materials stage) with a single detection step. The assay development stage can use multiple detection steps—it creates a "movie" of the cells responding through time, which this demonstrates and records the kinetics of the process. From this data, an optimal time is deduced for performing a single detection step in the actual screen. The single detection step will be at a time when the test compound has diffused part way across the site. Thus, there will be two geometrically distinct subpopulations of cells in the site at that time: one that has been exposed to the test compound and another that has not. Furthermore, the subpopulation that has been exposed, has been exposed progressively—those closer to the point source longer than those farther away. Thus, even though there is a single detection step, the activity, non-activity, and extent of activity of the cells will express the kinetics of the situation. In this manner, the present invention can detect activity in the cells with respect to their distance from the point source.

BRIEF DESCRIPTION OF THE DRAWINGS

FIG. 12A is a schematic diagram of a cross-section of one site of a multi-site assay apparatus, the site having two wells connected by a passageway for separately depositing cell suspension and test compound solution, according to an embodiment of the present invention.

FIG. 12B is a schematic diagram of a plan view of an exemplary site of the apparatus shown in FIG. 12B, according to an embodiment of the present invention.

DETAILED DESCRIPTION OF THE INVENTION

Figure 1:
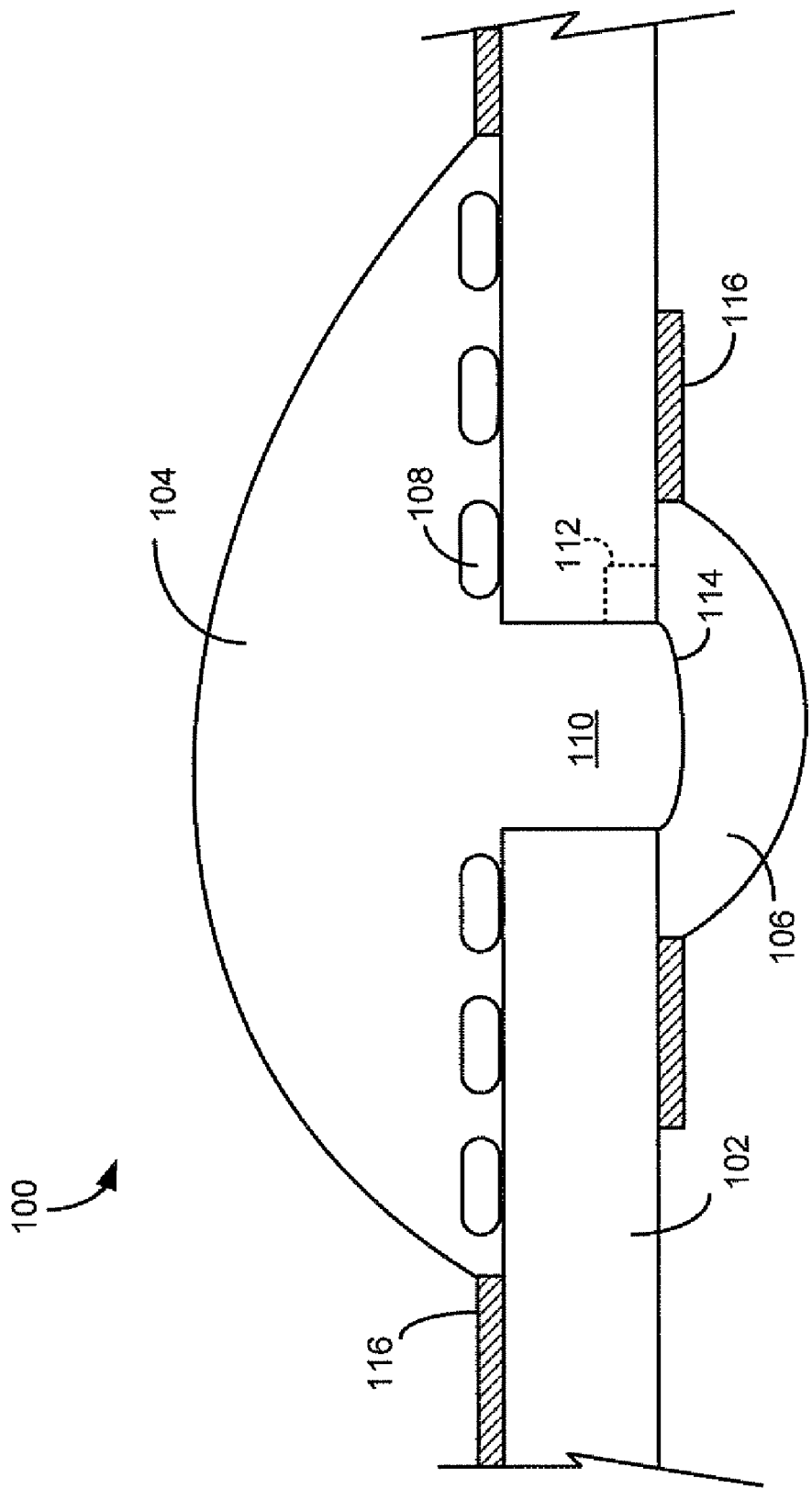
FIG. 1 is a schematic diagram of a cross-section of one site of a multi-site assay apparatus having a single film, according to an embodiment of the present invention.

FIG. 1 illustrates one site of a multi-site assay apparatus 100 according to an embodiment of the present invention. As shown, assay apparatus 100 includes a film 102, an opening 110 through film 102, cell suspension media 104 disposed on a first side of film 102 over opening 110, cells 108 of a cell suspension settled on the first side of film 102, and test compound solution 106 disposed on a second side of film 102 over opening 110. The test compound solution 106 initially contacts cell suspension media 104 at the meniscus 114 of cell suspension media 104 formed over opening 110 on the second side of film 102. Optionally, as shown in FIG. 1, film 102 could have hydrophobic coatings 116 to help keep cell suspension media 104 and test compound solution 106 in place.

After the initial contact between cell suspension media 104 and test compound solution 106, the test compound solution 106 diffuses into cell suspension media 104 through opening 110, and to the first side of film 102. The test compound solution 106 diffuses into cell suspension 104 from opening 110, thereby creating a concentration gradient emanating concentrically from opening 110. As this diffusion occurs, the test compound solution 106 reaches the cells 108 nearest opening 110 first and then eventually, over time, reaches the cells 108 farther away from opening 110. During this diffusion, apparatus 100 is periodically read to determine whether and when the cells 108 are responsive to the test compound solution 106. If the cells 108 are responsive, the effects are perceptible in stages, as the test compound solution 106 radially diffuses from opening 110. In this manner, the progressive response by cells 108 can yield both quantitative and kinetic data.

An embodiment of the present invention provides a method for performing a cell activity assay using the exemplary apparatus 100 shown in FIG. 1. According to this method, a cell suspension (containing cells suspended in a cell suspension media) is deposited onto the first side of film 102 over opening 110. The apparatus is then incubated, which allows the cells 108 to settle and adhere to the first side of film 102. The sites can then be read and recorded to provide a baseline reading of cells 108, or this step can be done immediately after the test solution is introduced.

The test compound solution 106 is then deposited on the second side of film 102 over opening 110. The test compound solution 106 can be deposited, for example, by inverting film 102 and pipetting onto the second side of film 102 by inverting a pin applicator and applying test compound solution 106 up onto the second side of film 102, by projecting the test compound upward, or by other appropriate means. Preferably, in depositing the cell suspension and test compound solution 106, the solutions are centered over opening 110.

With test compound solution 106 deposited on the second side of film 102, the test compound solution 106 is in contact with cell suspension media 104 at the opening 110. With this contact, test compound solution 106 begins diffusing into cell suspension media 104. The site is then read periodically to observe the effect of the test compound solution 106 on the cells 108 as this diffusion progresses. These readings detect, for example, cell elongation and orientation, other morphological changes, temperature changes, movement of molecules and structures within a cell, and electromagnetic changes. Detecting morphological changes involves, for example, examining the aspect ratio (length to width ratio) of the cells. Detecting cell orientation involves, for example, examining the orientation of the aspect ratio in relation to the opening from which the test compound solution is diffusing.

In the exemplary apparatus 100 shown in FIG. 1, cell suspension media 104 fills the opening 110, with a meniscus 114 formed on the end of opening 110 at the second side of film 110. This configuration provides an initial boundary (at meniscus 114) between the solutions. In this example, the cell suspension media 104 occupies opening 110 because the cell suspension is deposited first over the opening 110, fills the opening 110, and forms the meniscus 114 on the side of the opening 110 on the second side of the film 102. Preferably, as shown by the symbol 112, opening 110 is cut cleanly through film 102 such that the edge of the opening 110 at the second side is formed at a right angle, which helps opening 110 act as a hydrophobic barrier and from meniscus 114. Alternatively, opening 110 could be cut at non-right angles, for example, with a narrower width at either the first or the second side of film 102. As another option, instead of forming the opening 110 substantially perpendicular to the film 102 as shown in FIG. 1, opening 110 could be formed at an angle to the film 102.

In an embodiment of the present invention, opening 102 is a substantially circular opening. For example, in a film 102 that is approximately 25 microns thick, opening 110 could be an approximately 25 micron laser ablated hole. Cells 108 would typically be less than 25 microns in their largest dimension. In this way, a single cell 108 could not settle over opening 110 and completely block opening 110. To further avoid blocking opening 110, the cells 108 in cell suspension media 104 are preferably relatively sparse to reduce the chances of blocking opening 110. In an alternative embodiment, opening 110 is filled with a proteinaceous gel (e.g., a protein, such as collagen or keratin, forming an extracellular gel matrix) that prevents the cells 108 from passing from one side of film 102 to the other, but allows passage of the test compound solution 106 and controls diffusion into cell suspension media 104. This proteinaceous gel could also be applied to the surface of film 102 such that the cells 108 would settle on and adhere to the gel layer.

Figure 2:
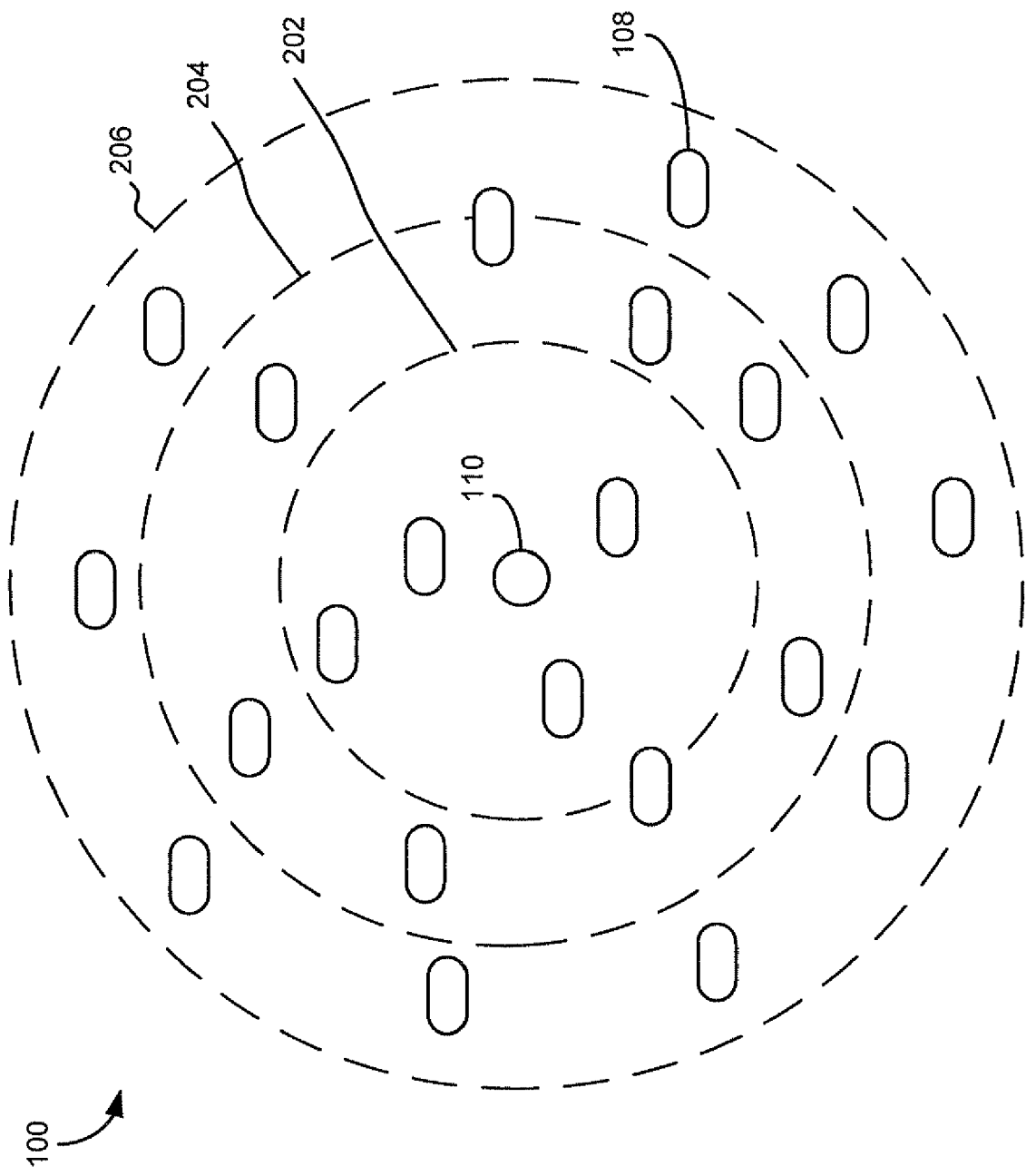
FIG. 2 is a schematic diagram of a top view of the assay apparatus of FIG. 1, showing a concentration gradient, according to an embodiment of the present invention.

With a substantially circular opening 110, test compound solution 106 diffuses into cell suspension media 104 concentrically from the opening 110. This radial diffusion creates a concentration gradient emanating from the opening 110 into cell suspension media 104 on the first side of film 102. FIG. 2 illustrates this concentration gradient, showing a representative top view of apparatus 100 looking down on cells 108 settled on film 102. Opening 110 is the point from which diffusion of the test compound solution 106 into the cell suspension media 104 begins. Therefore, the test compound solution 106 reaches the cells 108 nearest opening 110 first, as represented by those inside first gradient line 202. If these cells 108 are responsive to the test compound solution 106, then such response is detected in the cells within first gradient line 202, with the remaining cells 108 showing no response.

As the diffusion continues and apparatus 100 is periodically read, the test compound solution 106 reaches distances farther from the opening 110, as represented by the second gradient line 204 and the third gradient line 206. When the apparatus 100 is read at these increments of diffusion, cells within the respective gradient lines show a response (assuming the cells are responsive to the test compound solution). Moreover, all of the cells 108 within the outermost gradient line that the test compound solution 106 has reached may show varying degrees of response. For example, if the test compound solution 106 has reached the third gradient line 206, the cells 108 within the first gradient line 202 may show the most response and the cells between the second gradient line 204 and the third gradient line 206 may show the least response, with the cells 108 between the first gradient line 202 and the second gradient line 204 showing a response somewhere in between. In this manner, the present invention is able to provide not only quantitative data (e.g., number of cells effected) but also kinetic data (e.g., patterned response of the cells over time) and dose response data as the amount of test compound contacting cells further from the point of origin of diffusion decreases. In observing responses occurring outwardly in "rings," the present invention also removes doubt as to whether a response (or "hit") is detected, because the responses can be detected progressively in this "ring effect," Thus, the present invention can achieve coefficients of variation significantly lower than those of the prior art.

Figure 3:
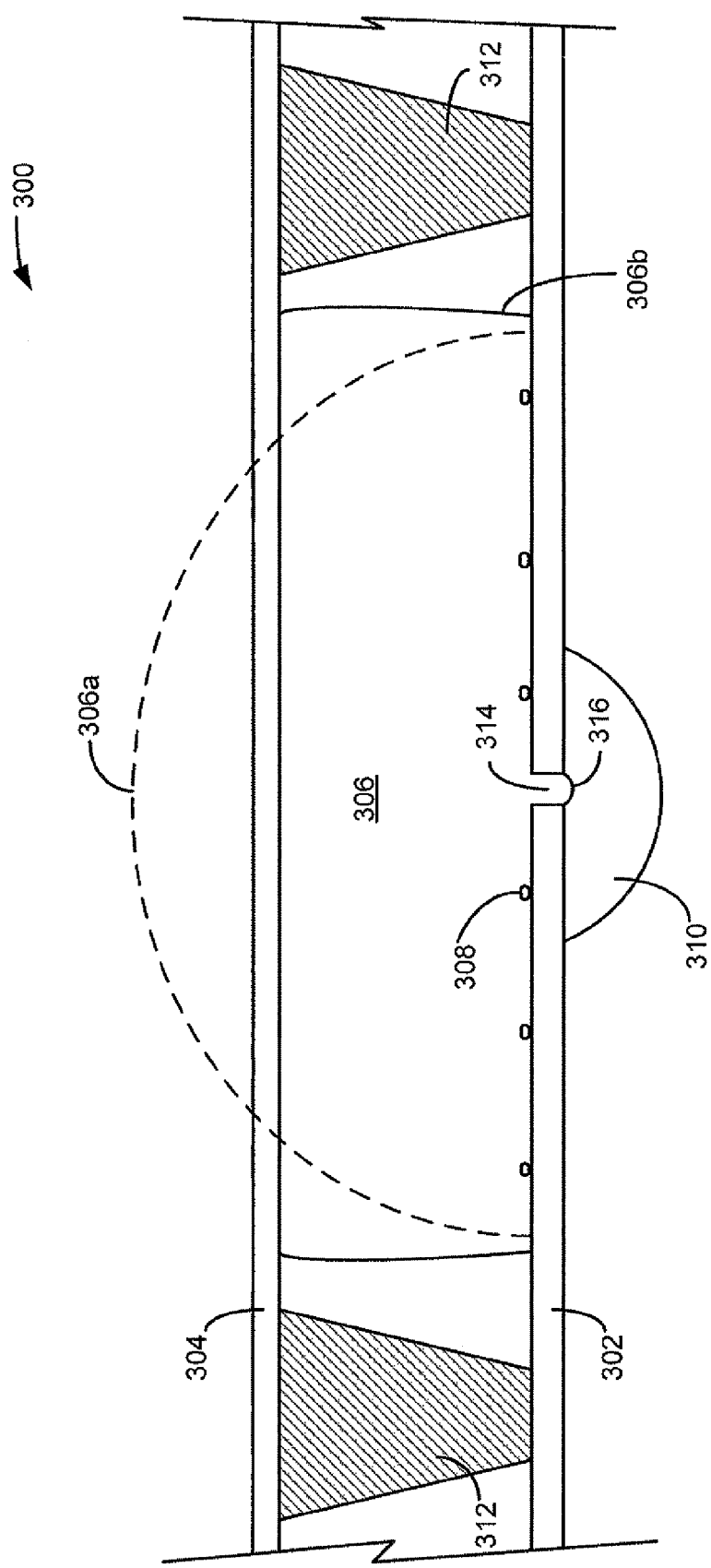
FIG. 3 is a schematic diagram of a cross-section of one site of a multi-site assay apparatus having two films, according to an embodiment of the present invention.

FIG. 3 illustrates one site of a multi-site assay apparatus 300 according to another embodiment of the present invention. Apparatus 300 is similar in most respects to the apparatus 100 of FIG. 1, except that apparatus 300 has a second film 304 over the cell suspension media 306. As shown, apparatus 300 includes a first film 302, an opening 314 through the first film 302, cell suspension media 306 disposed on a first side of first film 302 over opening 314, cells 308 settled on the first side of the first film 302, a test compound solution 306 disposed on a second side of film 302 over opening 314, and a second film 304 disposed over the cell suspension media 306. The second film 304 is preferably bonded to a plate 312 that supports the second film 304 and provides separation between the first film 302 and the second film 304.

The test compound solution 310 initially contacts cell suspension media 306 at the meniscus 316 of cell suspension media 306 formed over opening 314 on the second side of the first film 302. Optionally, although not shown in FIG. 3, the first film 302 could have hydrophobic coatings similar to those shown in FIG. 1, to help keep cell suspension media 306 and test compound solution 310 in place.

FIG. 3 shows a representative shape and position of cell suspension media 306 before and after the second film 304 is placed over the first film 302. Before the second film 304 is disposed over the first film 304, the cell suspension media 306 forms a drop, as shown by position 306a. After the second film 304 is in position over the first film 302, the second film 304 sandwiches the cell suspension media 306 in place, as shown by position 306b. Sandwiching the cell suspension media 306 provides a more stable captured drop free from evaporative effects. In addition, the flat surfaces of the second film 304 and the sandwiched cell suspension media 306 provide optically clear surfaces through which to take readings from above the second film 304 of apparatus 300 or from below. If a fluorescent reader is used, the excitation beam can be coaxial with the emission detector.

An embodiment of the present invention provides a method for performing a cell activity assay using the exemplary apparatus 300 shown in FIG. 3. According to this method, a cell suspension (containing cells suspended in a cell suspension media) is deposited onto the first side of the first film 302 over opening 314. The second film 304 is then placed over the first film 302 to sandwich the cell suspension in place. The apparatus 300 is incubated either before or after placing the second film 304, which allows the cells 308 to settle out of the cell suspension and adhere to the first side of the first film 302, leaving the cells 308 adhered to the first side and cell suspension media 306 covering the cells 308. With the cells 308 settled, optionally, the apparatus 300 can be read to provide a baseline reading of cells 308.

With the cell suspension media 306 in place, the test compound solution 310 is deposited on the second side of the first film 302 over opening 314. The test compound solution 310 can be deposited, for example, by inverting apparatus 300 and pipetting onto the second side of the first film 302, by inverting a pin applicator and applying test compound solution 310 up onto the second side of the first film 302, by projecting the test compound solution 310 upward, or by other appropriate means. Preferably, in depositing the cell suspension and test Compound solution 310, the solutions are centered over opening 314.

With test compound solution 310 deposited on the second side of the first film 302, the test compound solution 310 contacts cell suspension media 306 and begins diffusing into cell suspension media 306. Apparatus 300 is then read periodically, preferably through the second film 304, to observe the effect of test compound solution 310 on the cells 308 as this diffusion progresses concentrically outward. The second film 304 and the sandwiched cell suspension media 306 provide flat surfaces through which cells 308 can be more accurately and conveniently monitored for change.

Figure 4:
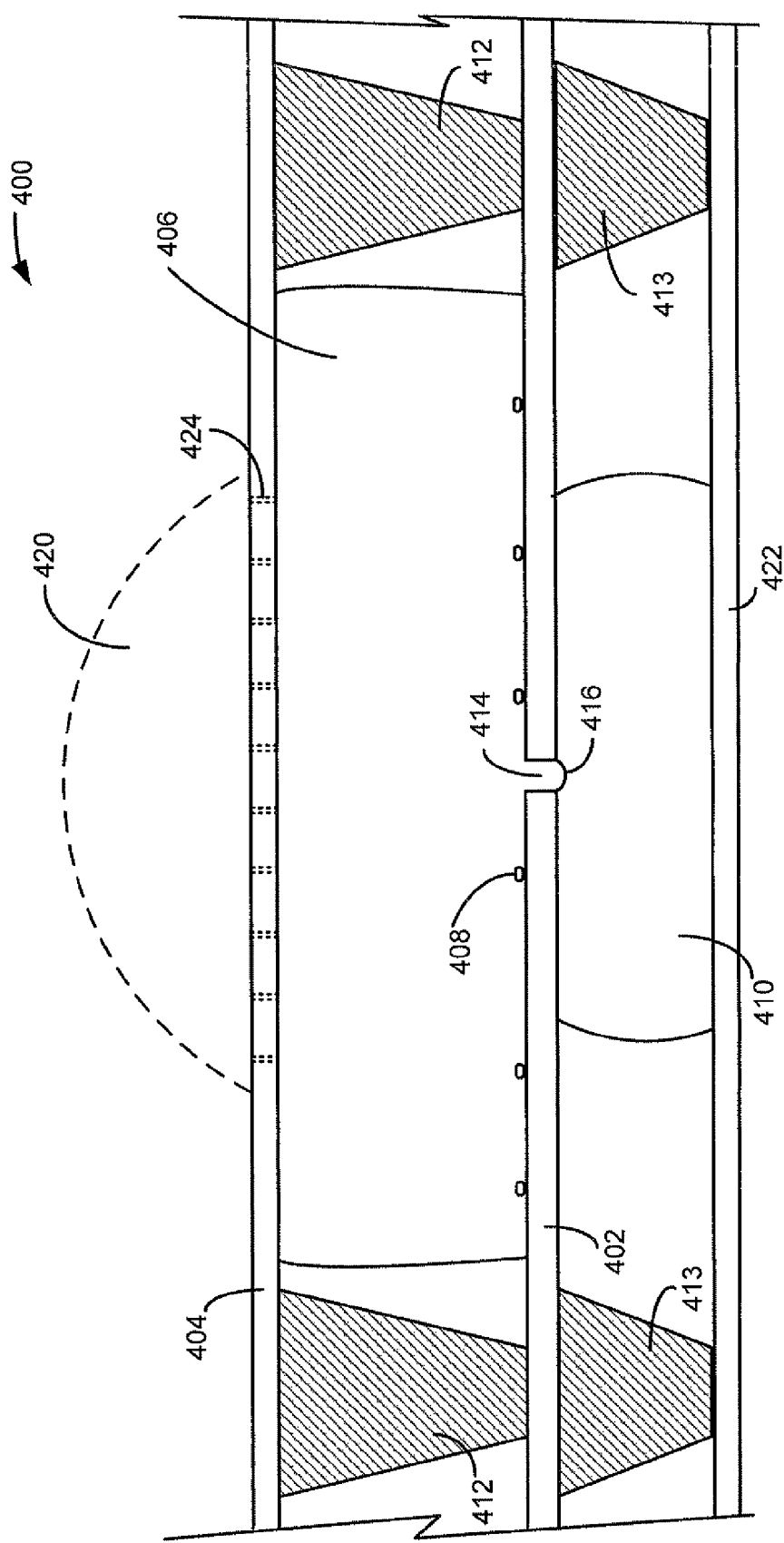
FIG. 4 is a schematic diagram of a cross-section of one site of a multi-site assay apparatus having three films, according to an embodiment of the present invention.

FIG. 4 illustrates one site of a multi-site assay apparatus 400 according to another embodiment of the present invention, which uses three films to sandwich both the cell suspension media and the test compound solution. As shown, apparatus 400 includes a first film 402 bonded to a first plate 413, a second film 404 bonded to a second plate 412, and a third film 422. The third film 422 can be bonded to the first plate 413 and/or another plate below (not shown). The first film 402 includes an opening 414. A cell suspension media 406 is disposed between the first film 402 and the second film 404, preferably centered over opening 414. Cells 408 are settled on a first side of the first film 402. A test compound solution 410 is disposed on a second side of film 402, between the first film 402 and the third film 422, and preferably centered over opening 414. The cell suspension media 406 also preferably forms a meniscus 416 on the second side of the first film 402 by capillary action.

Providing the third film 422 enables more options for assembling an assay. Specifically, the third film 422 provides a surface onto which the test compound solution 410 can be deposited. In this manner, the cell suspension (of which cell suspension media 406 is a part) can first be deposited on the first film 402 and sandwiched by the second film 404. Then, instead of inverting the assembled films 402 and 404 and depositing the test compound solution 410 onto the second side of the first film 402, or depositing the test compound solution 410 using an inverted pin applicator, the test compound solution 410 can be deposited onto the third film 422 in a separate operation. The third film 422, with a drop of the test compound solution 410 resting on it, is then brought up in contact with the first plate 413 such that the test compound solution 410 contacts the second side of the first film 402 and is sandwiched in place. In certain applications, sandwiching the test compound solution 410 in this manner may also beneficially push test compound solution 410 into the cell suspension media 406 and through opening 414, to facilitate the desired diffusion. In addition, sandwiching both the cell suspension media 406 and the test compound solution 410 reduces the effects that evaporation may have on assays. Additionally, the apparatus can be inverted.

Figure 10:
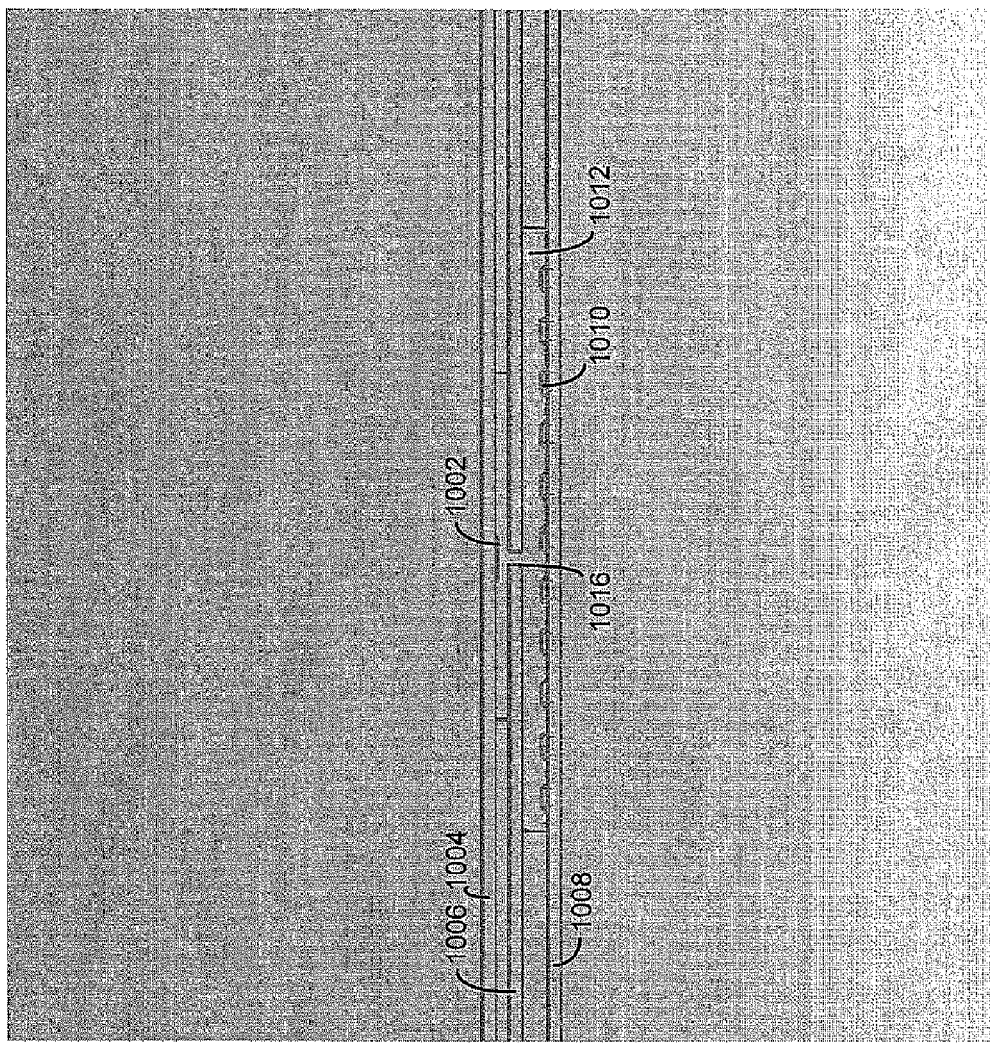
FIG. 10 is a schematic diagram of a cross-section of one site of a multi-site assay apparatus in which test compounds are applied to a film in very small drops and allowed to dry or are frozen, according to an embodiment of the present invention.

Alternatively, as shown in the apparatus of FIG. 10 (which is inverted with respect to the apparatus of FIG. 4 and which is described in more detail below), a test compound 1002 can be applied antecedently to the bottom side of the third film 1004. When the third film 1004 is applied to the apparatus over the middle film 1006, the media from the cell suspension wicks between the middle film 1006 and the third film 1004, dissolves test compound 1002 (or melts it if it is frozen) and initiates the diffusion of the test compound 1002 concentrically into the fluid between films 1006 and 1008.

In an alternative embodiment of FIG. 4, the second film 404 is a semi-permeable or porous filter membrane, instead of a non-permeable film. For example, the filter membrane could be fabricated from a film having pores, where the film can be made from a variety of materials including plastic, metal, glass, ceramic, organic material, or combinations thereof. As shown by the representative dotted lines in FIG. 4, the second film 404 can have pores 424 through which liquid can pass. A second media 420 is disposed on a side of the second film 404 opposite the side on which the cell suspension media 406 is disposed. The second media 420 passes through pores 424 to sustain cells 408 a longer duration than would otherwise be possible with the cell suspension media 406 alone. This second media 420 enables, for example, long term cell growth, proliferation, the formation of confluent cell layers, and differentiation, before initiation of contact with test compounds.

Although FIGS. 1-4 illustrate single assay or test sites, one of ordinary skill in the art would appreciate how the illustrated structures could be applied to multiple site apparatuses, for example, having 96, 384, or 1536 sites or to continuous strips of film. In such case, the structures or plates supporting the films (such as plate 312 of FIG. 3) would be lattices providing a through-hole for each site. This lattice plate or strip could be made of, for example, steel, plastic, or ceramics.

In an embodiment of the present invention, the films shown in FIGS. 1-4 are transparent Teflon™, e.g., 0.001 inch Teflon™. Of course, other materials could be used depending on the methods used to form openings in the films and the methods used to detect cell response.

The embodiments of FIGS. 1-4 illustrate a first film having a single opening through which the test compound solution can diffuse into the cell suspension media. Having a single opening is preferred for methods of detection that depend on the distance and orientation between the point of diffusion and the cells, such as detecting cell elongation and orientation and other morphological changes. For example, having a single diffusion source as opening 110 in FIG. 2 would simplify an analysis looking at how the cells 108 change shape or orient in a direction toward the single opening 110. With more than one opening, it may be difficult, although not impossible, to determine the effects that the multiple diffusion sources have on a certain cell. Nonetheless, the present invention does encompass first films having more than one opening. Other enhancements can be added, such as electrically conductive areas or lines, to provide the ability to check electrical resistance across cell layers to verify confluency.

As described above, the present invention allows the determination of cell activity by detecting changes in cells that are indicative of a response to a test compound solution and that occur well before a cell could migrate through a membrane. These changes include, for example, cell orientation, internal morphological changes, temperature variations, molecular movement within the cell, and electromagnetic changes. The most appropriate method of detecting these changes depends upon the types of compounds and cells that are under investigation. With any of these methods, the present invention provides the ability to detect the cell changes kinetically and without ambiguity, based on the test compound concentration gradients advancing concentrically and the cell activity progressing concentrically from the opening and into the cell suspension media.

As one example of detecting cell changes, an infrared reader could be used to monitor changes in the temperatures of cells. The cells could be immune cells, for example, that are exposed to compounds in the test compound solution that trigger a metabolic response in the immune cells. This metabolic reaction raises the temperature of the cells. Repeated scans by the infrared reader detect this rise in temperature. In addition, when a point diffusion source is used, the infrared reader can observe the ring effect caused by the concentration gradient, as cells closer to the test compound solution diffusion source respond first. The rise in temperature could continue as well, creating a temperature gradient among the rings of cells, which could be another source of kinetic data.

Figure 5:
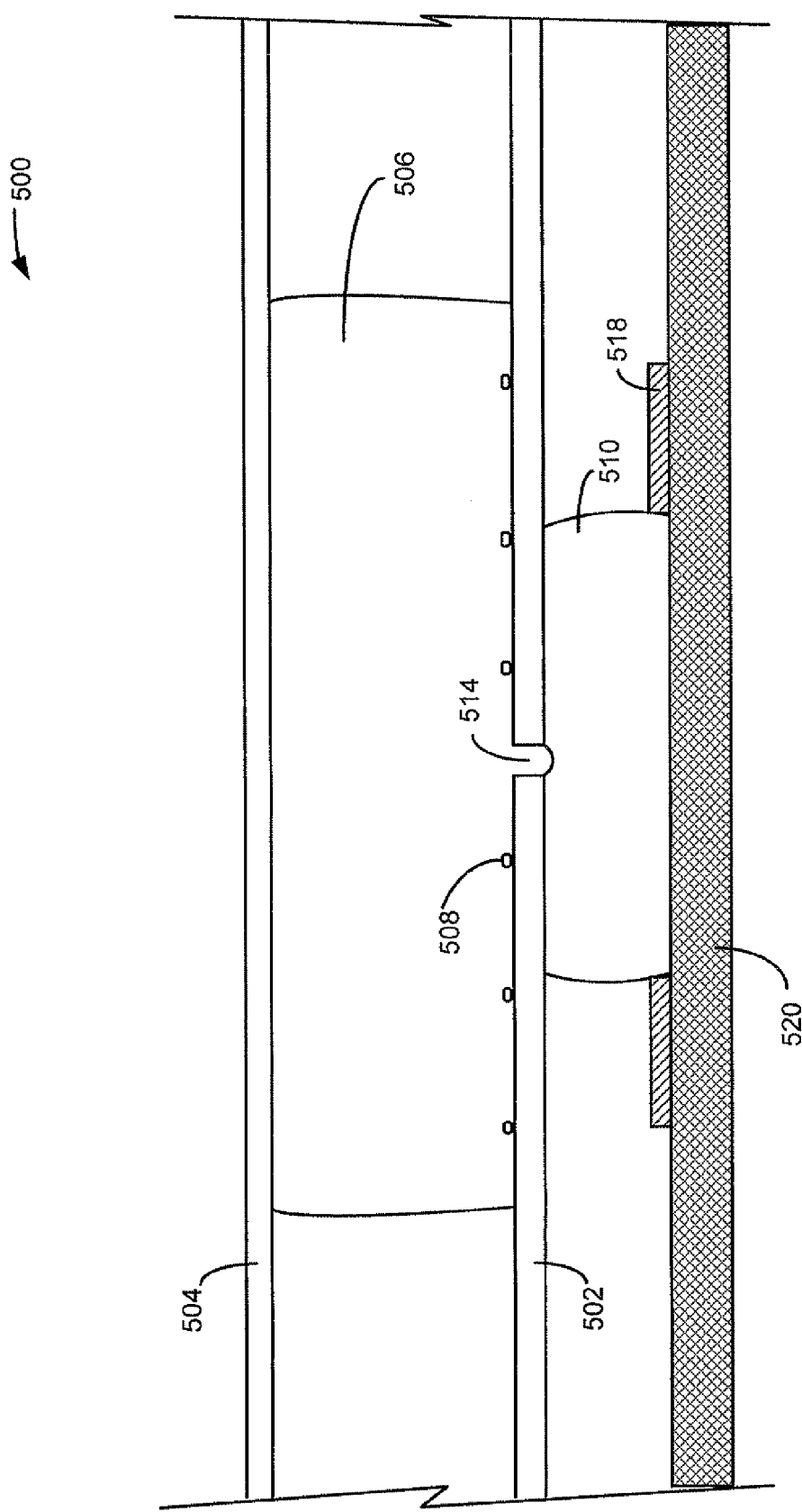
FIG. 5 is a schematic diagram of a cross-section of one site of a multi-site assay apparatus having a heat sink, according to an embodiment of the present invention.

In detecting cell response through temperature changes, an alternative embodiment of the present invention provides a heat sink 520 as shown in FIG. 5. This heat sink 520 establishes a constant background temperature, which facilitates consistent readings of temperatures. As shown in FIG. 5, an exemplary apparatus 500 according to this embodiment includes a cell suspension media 506 sandwiched between a first film 502 and a second film 504, and a test compound solution 510 sandwiched between the first film 502 and heat sink 520. The first and second films are preferably Teflon™ film. The first film 502 has an opening 514 through which the test compound solution 510 can diffuse into the cell suspension media 506. The heat sink 520 optionally has hydrophobic coatings 518 to keep test compound solution 510 in place. Heat sink 520 could be made of, for example, glass or anodized aluminum. Heat sink 520 ensures a constant temperature background against which infrared readings of the cells 508 can be taken. The apparatus can be constructed so that the sandwiching films of the cell suspension are in contact with the cells top and bottom and have insulating properties. This construction slows the rate of heat loss from a rise in temperature due to metabolic activity and allows detection systems time to record fluctuations.

As another example of detecting cell changes, a visible light reader could be used to monitor movement within fluorescently labeled cells. The cells could, for example, be tagged with green fluorescent protein (GPR). In this manner, well before a cell could orient itself, change in shape, or move toward the source of the test compound solution, the visible light reader could detect movement internal to the cell.

As another example of detecting cell changes, a microscopic detection system could be used to detect changes in cell shape and orientation. As a precursor to moving, the cells typically undergo morphological changes (e.g., changing their aspect ratio) and orient toward the source of test compound solution diffusion. Thus, these changes can be observed well before the cell moves. Examples of suitable microscopic detection systems are the confocal microscopy detection and imaging systems produced by Atto Bioscience of Rockville, Md.

As another example of detecting cell changes, an ultrasound detection system could be used to detect changes in cell shape and orientation.

In an alternative embodiment of the present invention, instead of providing a hole in the first film, through which test compound solution diffuses into the cell suspension media, a valve is formed in the film, which can be opened and closed to control the passage and diffusion of the test compound solution. As an example, the valve can be a slit cut into the film by, for example, piercing the film with a sharp wedge-shaped tip. The width of the wedge-shaped tip is preferably equal to the desired length of the valve. The valve is normally closed when no pressure differential exists across the film. When a pressure differential is applied across the film, the film bulges. This bulging opens the slit, thereby allowing test compound solution to pass through the slit.

Figure 6:
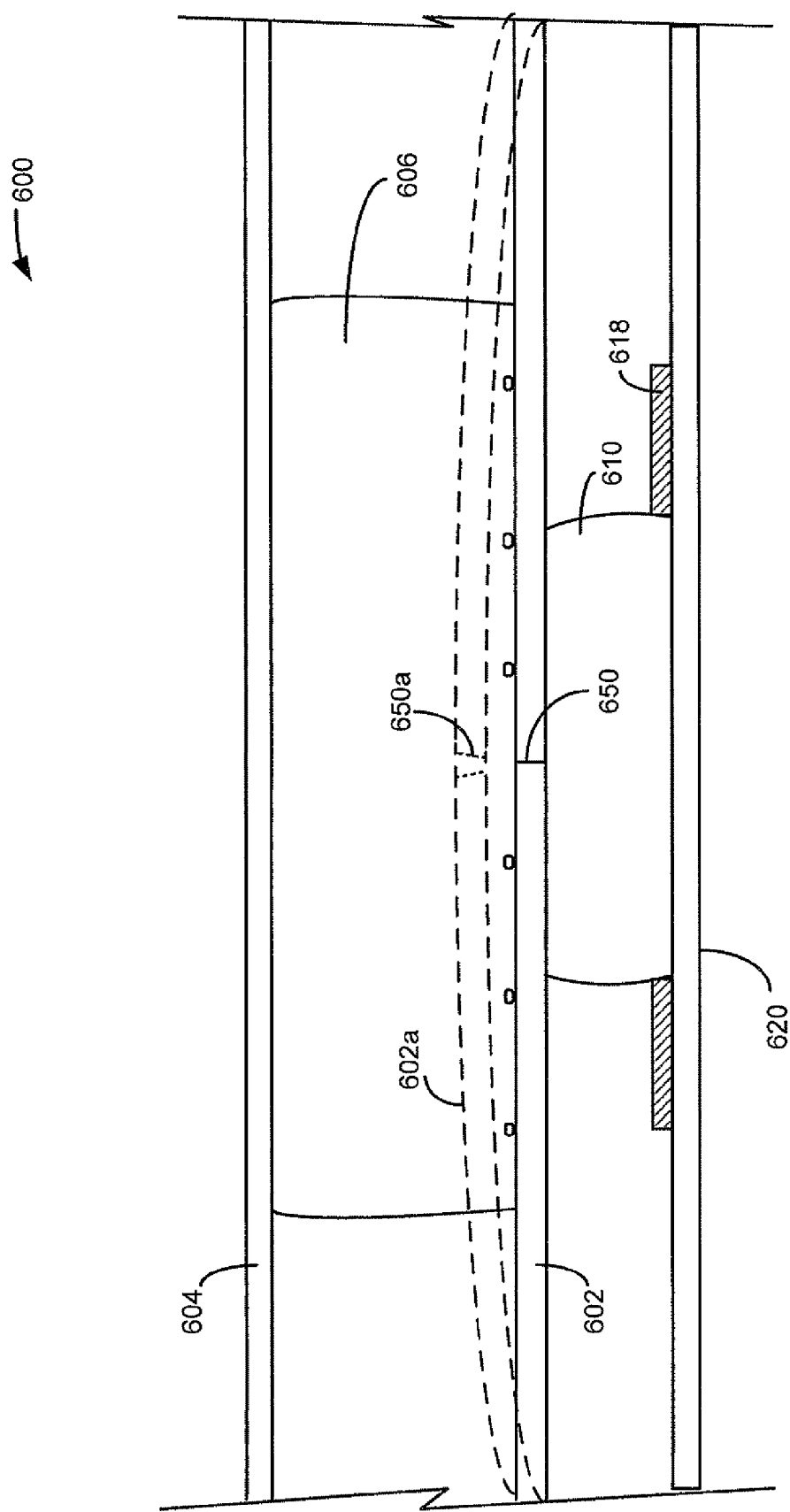
FIG. 6 is a schematic diagram of a cross-section of one site of a multi-site assay apparatus having a valve opening in the film between the cell suspension media and the test compound solution, according to an embodiment of the present invention.

In accordance with this alternative embodiment, FIG. 6 illustrates an apparatus 600 having a cell suspension media 606 sandwiched between a first film 602 and a second film 604 and a test compound solution 610 sandwiched between the first film 602 and a third film 620. Although not shown, plates could be included to support films 602, 604, and 620. The first film includes a slit 650 that is normally closed, preventing passage of the test compound solution 610 into the cell suspension media 606. When a pressure differential is applied across the first film 602, however, the slit opens as shown by bulging first film 602a and open slit 650a. This pressure differential can be achieved, for example, by raising the pressure in the area between the first film 602 and the third film 620, by reducing the pressure in the area between the first film 602 and the second film 604, or by reducing the ambient pressure outside of apparatus 600. By controlling the relative pressures, and opening and closing slit 650, a user can control the amount of test compound solution introduced into the cell suspension media at the valve. This process can be repeated one or more times with detection of cell activity between cycles or continuously. This apparatus and method allow data to be collected on dose response to a compound.

Figure 7:
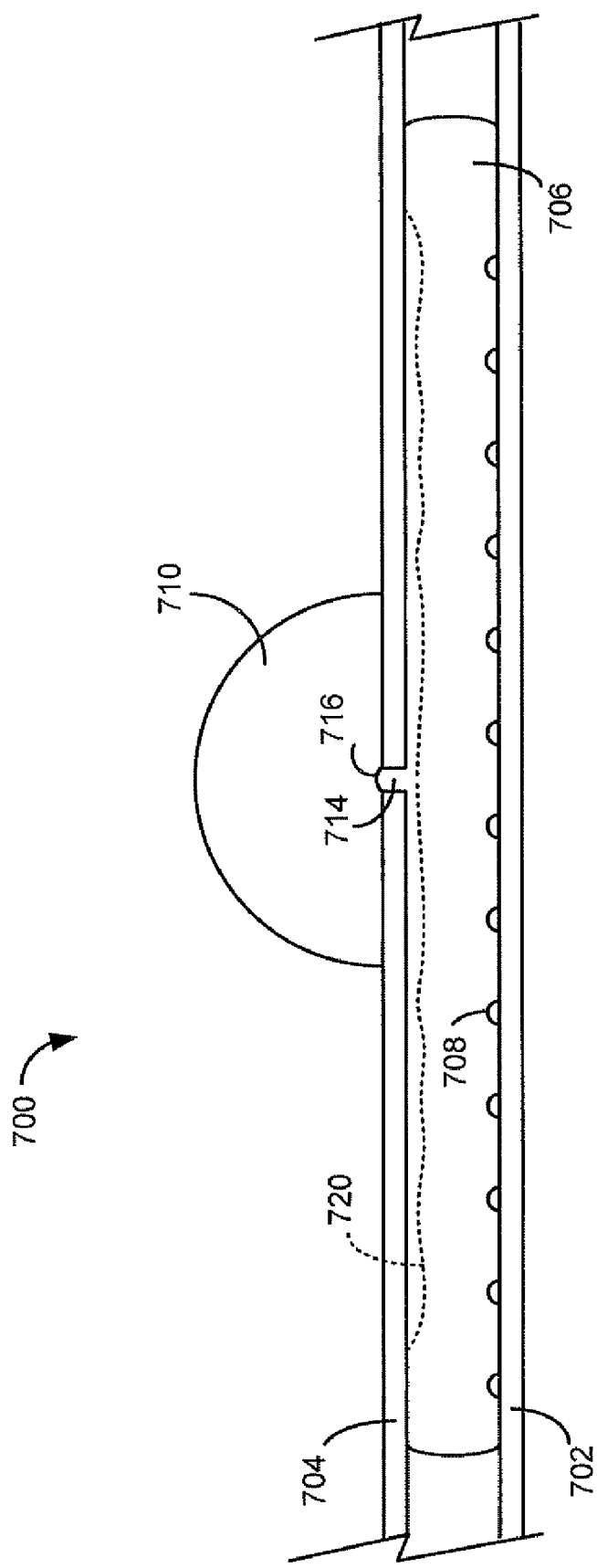
FIG. 7 is a schematic diagram of a cross-section of one site of a multi-site assay apparatus in which the cells and test compound solution are deposited on two different films, according to an alternative embodiment of the present invention.

FIG. 7 illustrates another embodiment of the present invention, which deposits the cells and test compound solution on two different films (as opposed to depositing the cells and the test compound solution on opposite sides of the same film, as in FIGS. 1-6). As shown, an apparatus 700 according to this embodiment includes a first film 702, cells 708 settled on the first film 702, a cell suspension media 706 surrounding cells 708 and sandwiched between first film 702 and a second film 704, and a test compound solution 710 disposed on the second film 704 over an opening 714 in second film 704. The test compound solution 710 initially contacts cell suspension media 706 at the meniscus 716 of cell suspension media 706 formed in or over opening 714.

An embodiment of the present invention provides a method for performing a cell activity assay using the exemplary apparatus 700 shown in FIG. 7. According to this method, a cell suspension (containing cells suspended in a cell suspension media) is deposited onto film 702. The film 702 is then incubated, which allows the cells 708 to settle and adhere to the film 702, leaving the cells 708 adhered to the film 702 and the cell suspension media 706 covering the cells 708. Optionally, the cells 708 on film 702 are then read to provide a baseline reading.

A second film 704 is then placed over cell suspension media 706 with opening 714 disposed (and preferably centered) over cell suspension media 706. With cell suspension media 706 sandwiched in place between films 702 and 704, a portion of cell suspension media 706 is drawn into opening 714 by capillary action and forms meniscus 716.

A test compound solution 710 is then deposited on the side of film 704 opposite the side on which cell suspension media 706 is disposed. Test compound solution 710 is preferably centered over opening 714.

With test compound solution 710 deposited on film 704, the test compound solution 710 is in contact with cell suspension media 706 at the opening 714. With this contact, test compound solution 710 begins diffusing into cell suspension media 706. The site is then read periodically to observe the effect of the test compound solution 710 on the cells 708 as this diffusion progresses. These readings detect, for example, cell elongation and orientation, other morphological changes, temperature changes, movement of molecules and structures within a cell, and electromagnetic changes.

In an alternative embodiment of FIG. 7, the test compound solution 710 of FIG. 7 is set in a gel, such as a proteinaceous gel. This gel helps control the rate of release of the test compound solution and the diffusion of the test compound solution into cell suspension media 706. In this manner, a researcher can slow the diffusion of the test compound solution 710 into the cell suspension media 706 as appropriate for a particular study and for the means used to detect cell activity.

In another alternative embodiment of FIG. 7, the test compound solution 710 is contained in a sintered material that holds the test compound solution 710 and releases it in a controlled manner similar to the controlled release provided by a gel.

In another alternative embodiment of FIG. 7, the test compound solution 710 is a solution and the opening 714 of film 704 is occluded with a gel, such as a proteinaceous gel. In this embodiment, the test compound solution 710 must pass through the gel to reach and diffuse into the cell suspension media 706. The gel in opening 714 prevents flow of the test compound solution into the cell suspension media and also helps control the rate of diffusion.

In another alternative embodiment of FIG. 7, the test compound solution 710 is frozen when it is initially deposited on film 704. Then, as the frozen compound solution 710 melts, it gradually enters opening 714 and diffuses into the cell suspension media 706. Using a frozen test compound solution 710 can therefore prevent flow and help control the diffusion into the cell suspension media 706.

In another alternative embodiment of FIG. 7, the test compound solution 710 is applied in two steps. First, a dry or freeze-dried compound is deposited on film 704. Second, a solution is added to the dry or freeze-dried compound. The compound then gradually dissolves to become the test compound solution 710. As this gradual dissolving occurs, the test compound solution 710 gradually diffuses into the cell suspension media 706. Alternatively, instead of adding a solution to the dry or freeze-dried compound, the cell suspension media 706 could be used to gradually dissolve the compound in suitable applications, perhaps also with the aid of moving film 704 (e.g., in ways akin to those described above in reference to FIG. 6) to promote mixing of the compound and the cell suspension media 706.

As one of ordinary skill in the art would readily appreciate, the above-described alternative embodiments of FIG. 7, which help control the rate of release of the test compound solution and the diffusion of the test compound solution into cell suspension media, could be applied to other embodiments of the present invention besides that of FIG. 7.

In another alternative embodiment of FIG. 7, apparatus 700 is adapted for assays that study the diffusion rate of members of a compound library through various confluent cell layers, e.g., endothelial or epithelial cell layers. In this embodiment, a cell layer 720, as represented by the dotted lines, is disposed on the side of film 704 opposite the side on which the test compound solution 710 is disposed. Cell layer 720 also covers opening 714. The test compound solution 710 contacts cell layer 720 (perhaps causing changes in cell layer 720) and diffuses into cell suspension media 706 to reach and cause changes in cells 708.

Figure 8:
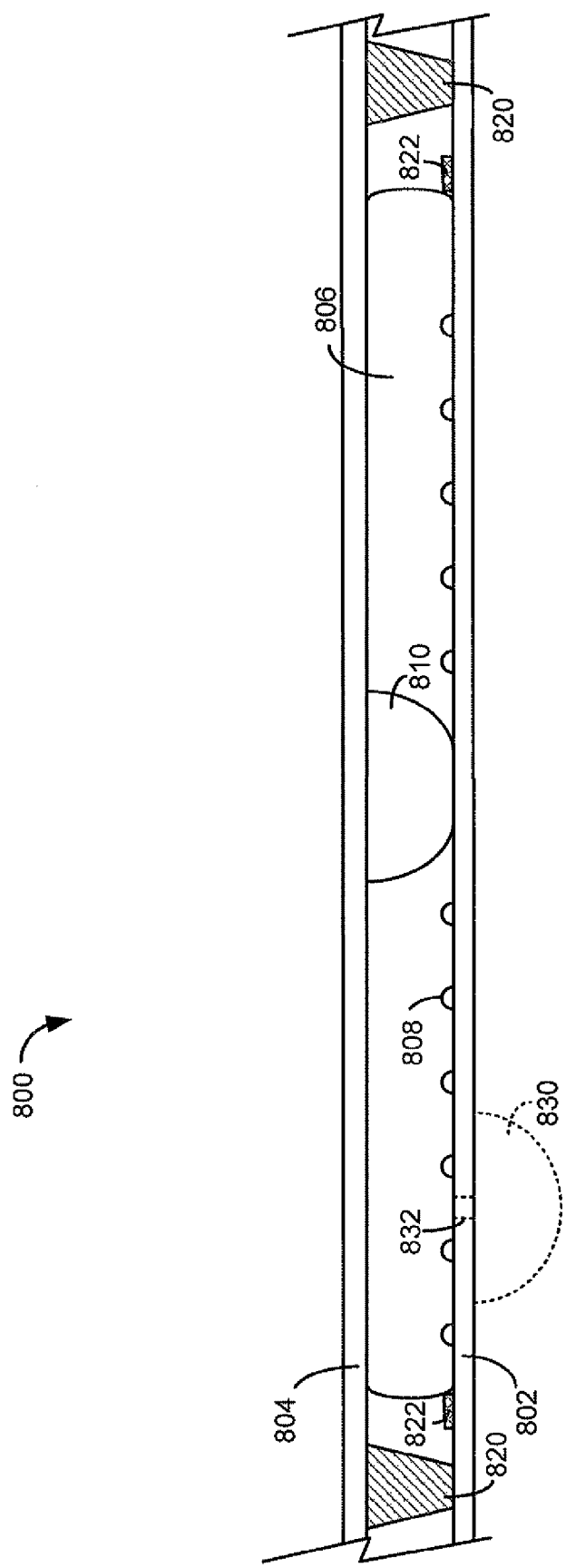
FIG. 8 is a schematic diagram of a cross-section of one site of a multi-site assay apparatus in which a test compound solution is set in a material that slowly releases the test compound solution, and the material and test compound solution are surrounded by the cell suspension media, according to an alternative embodiment of the present invention.

FIG. 8 illustrates another embodiment of the present invention, in which a test compound solution is set in a material (e.g., a gel or a sintered material) that slowly releases the test compound solution, and the material and test compound solution are surrounded by the cell suspension media. As shown, an apparatus 800 according to this embodiment includes a first film 802, cells 808 settled on the first film 802, a cell suspension media 806 surrounding cells 808 and sandwiched between first film 802 and a second film 804, and a test compound solution gel 810 disposed within the cell suspension media 806 and between first film 802 and second film 804. The gel 810 slowly releases the test compound solution, which contacts and diffuses into cell suspension media 806.

As shown in FIG. 8, a support structure 820 can be provided to separate the first film 802 from the second film 804 at a desired distance. Alternatively, instead of using structure 820, the test compound solution gel 810 itself can separate the first film 802 and the second film 804 provided the test compound solution gel 810 has a suitable size and consistency, perhaps also aided by a hydrophobic coating 822 for further support. As another alternative, the surface tension of the cell suspension media 806 could separate the first film 802 and the second film 804 at a desired distance.

An embodiment of the present invention provides a method for performing a cell activity assay using the exemplary apparatus 800 shown in FIG. 8. According to this method, a cell suspension (containing cells suspended in a cell suspension media) is deposited onto first film 802. The first film 802 is then incubated, which allows the cells 808 to settle and adhere to the first film 802, leaving the cells 808 adhered to the first film 802 and the cell suspension media 806 covering the cells 808. Optionally, the cells 808 on first film 802 are then read to provide a baseline reading.

Then, the test compound solution gel 810 is deposited on the second film 804. For example, a gel could be first deposited on the second film 804, and then the test compound solution deposited on the gel. Alternatively, the test compound solution could already be mixed with gel, and then deposited on the second film 804 and allowed to gel (or dry).

With the test compound solution gel 810 deposited on the second film 804, the second film 804 is inverted and placed over first film 802. Preferably, test compound solution gel 810 is centered over cell suspension media 806. Optionally, before placing second film 804 over first film 802, a portion of fluid is removed from cell suspension media 806 if too much cell suspension media 806 is present. The surface tension of the cell suspension media 806, the thickness of the gel 810, and/or the structure 820 supporting films 802 and 804 determine the distance between the surfaces of the films and thus the thickness of the cell suspension media 806.

With the first film 802 and the second film 804 together, the test compound solution gel 810 is surrounded by cell suspension media 806. Test compound solution therefore gradually releases from the test compound solution gel 810 and diffuses into cell suspension media 806. The site is then read periodically to observe the effect of the test compound solution on the cells 808 as this diffusion progresses.

In an alternative embodiment of FIG. 8, a test compound solution is frozen when it is initially deposited on second film 804 and brought into contact with cell suspension media 806. Then, as the frozen compound solution melts, it gradually diffuses into the cell suspension media 806. Using a frozen test compound solution can therefore help control the diffusion into the cell suspension media 806.

In another alternative embodiment of FIG. 8, a test compound solution is applied in two steps to second film 804. First, a dry or freeze-dried compound is deposited on second film 804. Second, a solution is added to the dry or freeze-dried compound. The solution and dissolving compound are then brought in contact with the cell suspension media 806. As the compound continues to dissolve, test compound solution gradually diffuses into the cell suspension media 806. Alternatively, instead of adding a solution to the dry or freeze-dried compound, the cell suspension media 806 could be used to gradually dissolve the compound in suitable applications, perhaps also with the aid of moving film 804 (e.g., in ways akin to those described above in reference to FIG. 6) to promote mixing of the compound and the cell suspension media 806.

In another alternative embodiment of FIG. 8, apparatus 800 is adapted for assays that study the effects of test compound solution inhibitors on known cell activity generators. In this embodiment, an inhibitor test compound solution 830, as represented by the dotted line, is disposed on a side of first film 802 opposite the side on which the cell suspension media 806 and test compound solution gel 810 are disposed. An opening 832, as represented by the dotted lines, is disposed in the first film 802, over which the inhibitor test compound solution 830 is disposed. (Optionally, opening 832 and inhibitor test compound solution 830 could be disposed at second film 804, instead of first film 802.)

The test compound solution gel 810 is a known cell activity generator. Therefore, a researcher can anticipate the release of the test compound solution from the gel, the diffusion of the test compound solution into cell suspension media 806, and the response of the cells 808 to the test compound solution. Acting against this response, the inhibitor test compound solution 830 contacts the cell suspension media 806 in or around opening 832 and diffuses into the cell suspension media 806. As the inhibitor test compound solution 830 reaches the cells 808 closest to opening 832, those cells 808 stop responding to the known cell activity generator (test compound solution gel 810), if the cells 808 are responsive to the inhibitor test compound solution 830. Accordingly, a researcher can observe the effects of the inhibitor test compound solution 830 as the two diffusion gradients (of the known cell activity generator and the inhibitor) overlap.

As one of ordinary skill in the art would appreciate, this alternative embodiment of FIG. 8, using an inhibitor test compound solution, could be applied to other embodiments discussed above, such as FIG. 7. For example, in FIG. 7, an inhibitor test compound solution could be deposited on film 702 on a side opposite the side on which cell suspension media 706 is disposed. An opening would be provided in film 702 through which the inhibitor test compound solution would diffuse into cell suspension media 706. The test compound solution gel 710 would be the known cell activity generator. As another example, in FIG. 8, both the inhibitor test compound solution and the known cell activity generator compound solution could be set in gels and disposed within cell suspension media 806 apart from each other. The inhibitor and generator solutions would diffuse into the cell suspension media 806, creating the overlapping diffusion gradients discussed above.

Figure 9:
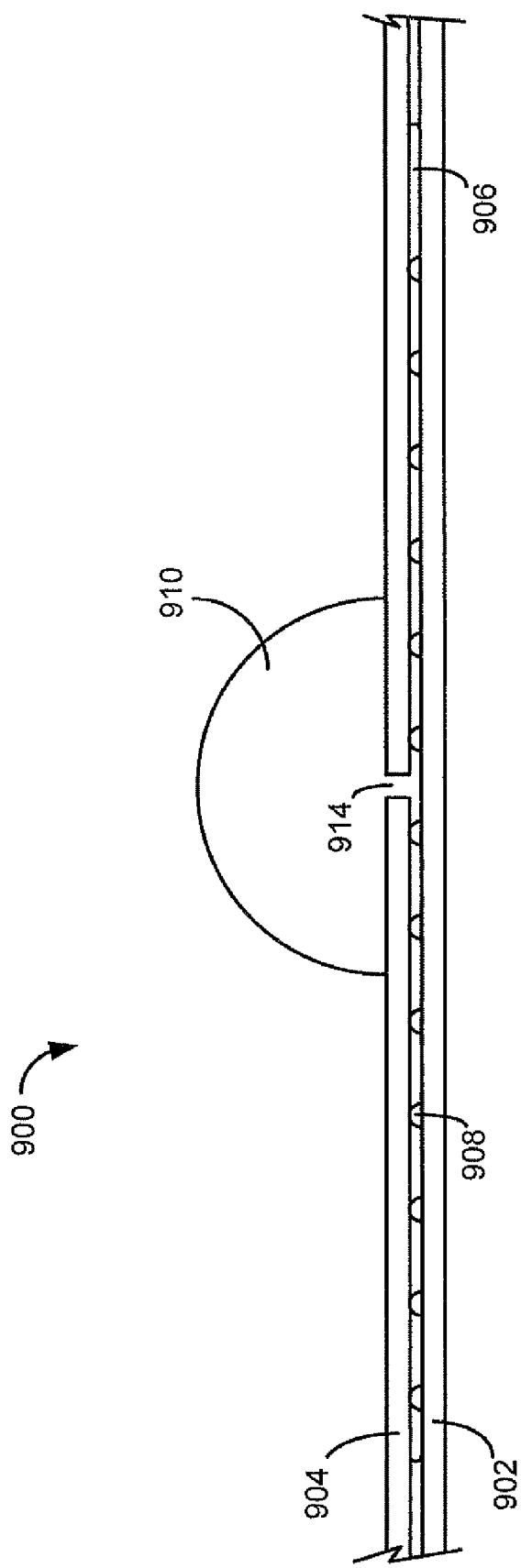
FIG. 9 is a schematic diagram of a cross-section of one site of a multi-site assay apparatus in which cells are sandwiched between two films, according to an embodiment of the present invention.

FIG. 9 illustrates an embodiment of the present invention in which the cells being studied are sandwiched between two films. As shown, an apparatus 900 according to this embodiment includes a first film 902, a second film 904, cells 908 sandwiched between the first film 902 and the second film 904, a cell suspension media 906 surrounding cells 908, and a test compound solution gel 910 disposed on the second film 904 over an opening 914 in the first film 904. In a particular implementation of this embodiment, the first film 902 is about 0.0010 inches thick, the second film 904 is about 0.0010 inches thick, and the distance between the films 902 and 904 (or height of the cells 908) is about 0.0003 inches.

An embodiment of the present invention provides a method for performing a cell activity assay using the exemplary apparatus 900 shown in FIG. 9. According to this method, a cell suspension (containing cells suspended in a cell suspension media) is deposited onto film 902. The film 902 is then incubated, which allows the cells 908 to settle and adhere to the film 902, leaving the cells 908 adhered to the film 902 and the cell suspension media 906 covering the cells 908. Optionally, the cells 908 on film 902 are then read to provide a baseline reading.

A second film 904 is then placed over cell suspension media 906 with opening 914 disposed (and preferably centered) over cell suspension media 906. The second film 904 is sucked, or forced with pressure, into contact with the tops of cells 908. This contact insulates the cells 908 from the cell suspension media 906 and allows imaging from either side (i.e., facing first film 902 or second film 904). Insulating the cells 908 is helpful for detecting temperature variations in the cells due to metabolic changes. By insulating cells 908 and reducing the surface area of the cells 908 that is exposed to the cell suspension media 906, metabolic heat gains of the cells 908 can be sustained and detected.

A test compound solution gel 910 is then deposited on second film 904 over (preferably, centered over) the opening 914. The test compound solution gel 910 is in contact with cell suspension media 906 at the opening 914. With this contact, test compound solution begins diffusing into cell suspension media 906. The site is then read periodically to observe the effect of the test compound solution on the cells 908 as this diffusion progresses. These readings detect, for example, cell elongation and orientation, other morphological changes, temperature changes, movement of molecules and structures within a cell, and electromagnetic changes.

In sandwiching the cells 908, this configuration is especially conducive to infrared detection systems. Indeed, infrared detection can provide a three-dimensional image of the sandwiched cells 908, making the detection of any cell activity even more sensitive. Optionally, the film opposite the film through which the infrared detection passes is coated with a reflective surface (e.g., aluminum) to reflect the infrared light and further enhance the imaging. Thus, for example, in FIG. 9, if the infrared detector is disposed beneath first film 902, the top side of the second film 904 could be coated with a reflective material.

In another alternative embodiment of FIG. 9, rather than a gel, other means are used to hold the test compound solution and release it in a controlled manner to diffuse into the cell suspension media 906. For example, as described above, these other means could include setting the test compound solution in a sintered material, occluding the opening 914 with a gel, depositing the test compound solution in a frozen form, or depositing the test compound in a dry or freeze-dried form.

In another embodiment of the invention illustrated in FIG. 10, the test compounds are applied to a film in very small drops (picoliter to nanoliter volumes) and allowed to dry or are frozen. Cell suspension is applied to the bottom film 1008 and sandwiched between the bottom film 1008 and middle film 1006, and the cells 1010 are allowed time to adhere (if they are adherent). The third film 1004 is then applied or laminated to the second film 1006 with the test compound 1002 approximately over the hole 1016 in the middle film 1006. The cell suspension media 1012 wicks by capillary action between the top of the middle film 1006 and the bottom of the top film 1004, and dissolves or melts the test compound 1002. The test compound 1002 then diffuses through the hole 1016 in the middle film 1006 and then concentrically between the bottom film 1008 and the middle film 1006. Multiple compounds corresponding to multiple holes in the middle film can be used in one site to detect synergistic or inhibitory effects.

Figure 11A:
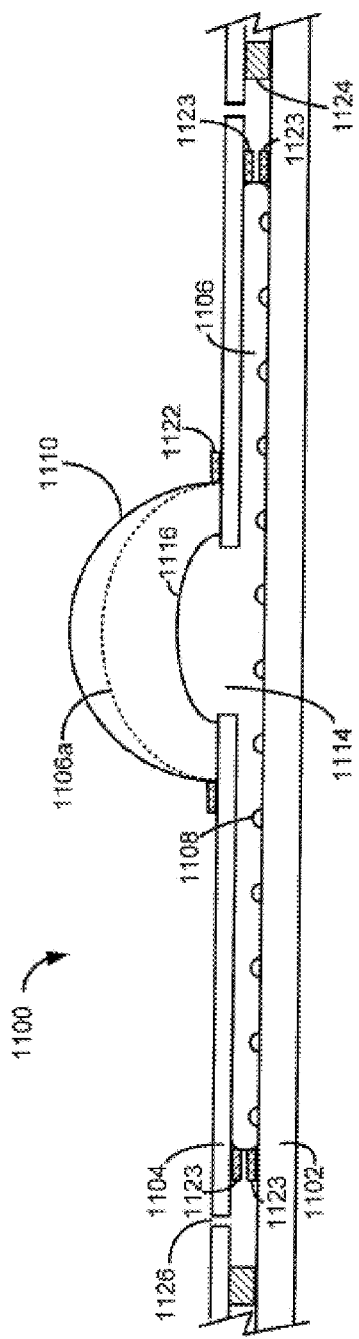
FIG. 11A is a schematic diagram of a cross-section of one site of a multi-site assay apparatus in which cell suspension and test compound solution are deposited sequentially on the same side of a film over an opening in the film, according to an embodiment of the present invention.

FIG. 11A illustrates another embodiment of the present invention, in which cell suspension and test compound solution are deposited sequentially on the same side of a film over an opening in the film. As shown, an apparatus 1100 according to this embodiment includes a transparent substrate 1102 and a film 1104. Substrate 1102 and film 1104 are connected and held apart from each other by, for example, a support structure or, as shown in FIG. 11A, adhesive 1124. Substrate 1102 is preferably made of glass or any other material that is transparent to the means for detection (e.g., transparent to electromagnetic radiation) and has surface characteristics that enable solutions to wick or flow easily. Substrate 1102 could also be a film with suitable surface characteristics. Film 1104 defines an opening 1114. Cells 1108 are settled on the substrate 1102 and a cell suspension media 1106 surrounds cells 1108 and is sandwiched between substrate 1102 and a film 1104. A test compound solution 1110 is disposed on the film 1104 and over cell suspension media 1106 and opening 1114 in film 1104. The test compound solution 1110 initially contacts cell suspension media 1106 at the meniscus 1116 of cell suspension media 1106 formed in or over opening 1114.

Apparatus 1100 can also include selectively applied hydrophobic coatings 1122 to help hold cells 1108, cell suspension media 1106, and test compound solution 1110 stationary, or in place. For example, as shown in FIG. 11A, the upper surface of film 1104 can have hydrophobic coatings 1122 that hold solutions in place over opening 1114. Similarly, the bottom surface of film 1104 and the upper surface of substrate 1102 can have selectively applied hydrophobic coatings 1123 that contain solutions within the site, but still allow air to pass.

An embodiment of the present invention provides a method for performing a cell activity assay using the exemplary apparatus 1100 shown in FIG. 11A. This exemplary method is performed on apparatus 1100 with substrate 1102 and film 1104 already assembled as shown in FIG. 11A. According to this method, a cell suspension (containing cells suspended in a cell suspension media) is deposited onto the upper surface of film 1104, preferably centered over opening 1114. Hydrophobic coatings 1122 assist in holding the cell suspension in place and centering it over opening 1114. The initial placement of the cell suspension is represented in FIG. 11A by the dotted line 1106a.

After this initial placement, the cell suspension flows through opening 1114, into the space between substrate 1102 and film 1104, and up to the hydrophobic barriers 1123. The dimensions of the space can create a wicking action that draws the cell suspension into the site and to the hydrophobic barriers 1123. In addition, to further promote the flow of the cell suspension into the space, air pushed by the cell suspension can be released through hydrophobic barriers 1123 and out of the site through a vent or vents, such as vent 1126 defined by film 1104. After cell suspension reaches hydrophobic barriers 1123, flow ceases and the cell suspension assumes a stationary position as represented by meniscus line 1116. Limiting the flow of the cell suspension promotes the settling out of cells and establishes a stationary media across which uniform diffusion can occur. At this point, apparatus 1100 can be incubated if necessary for cells 1108 to settle out of the cell suspension and adhere to substrate 1102, leaving the adhered cells 1108 surrounded by stationary cell suspension media 1106. Optionally, the cells 1108 on substrate 1102 are then read to provide a baseline reading.

A test compound solution 1110 is then deposited into or on top of cell suspension media 1106, on the upper surface of film 1104, preferably centered over opening 1114. Test compound solution 1110 contains the compound to be screened for cell activity. Hydrophobic coatings 1122 assist in holding test compound solution 1110 in position and centered over opening 1114. Although not shown in FIG. 11A, at this point, with the cell suspension and test compound solution 1110 deposited, a lid could be placed over film 1104 to seal the site and limit evaporation of the solutions.

With test compound solution 1110 deposited on film 1104 and into or on cell suspension media 1106, the test compound solution 1110 is in contact with cell suspension media 1106 at meniscus 1116. With this contact, test compound solution 1110 begins diffusing into cell suspension media 1106. The positional stability of the solutions, as provided by the hydrophobic barriers, promotes an even and measurable concentric diffusion across the site. The site is then read periodically to observe the effect of the test compound solution 1110 on the cells 1108 as this diffusion progresses. These readings detect, for example, cell elongation and orientation, other morphological changes, temperature changes, movement of molecules and structures within a cell, and electromagnetic changes.

In an exemplary implementation of the embodiment of FIG. 11A, the single site of FIG. 11A is part of a 96-site apparatus, in which each site is approximately 9×9 mm square and the area within each site that is defined by hydrophobic barriers 1123 is approximately 7×7 mm square. The distance between substrate 1102 and film 1104 is approximately 10-200μ. The volume of the site defined by the hydrophobic barriers 1123 is approximately 1-5 μl. With this configuration, experiments have shown that between approximately 1 μl and approximately 5 μl of cell suspension can be deposited in the site and that altered cell activity can be observed in the cells 1108 nearest the hydrophobic barriers 1123 within about 15-40 minutes after a compound solution with known cell activity inducing properties has been applied to the site.

Figure 11B:
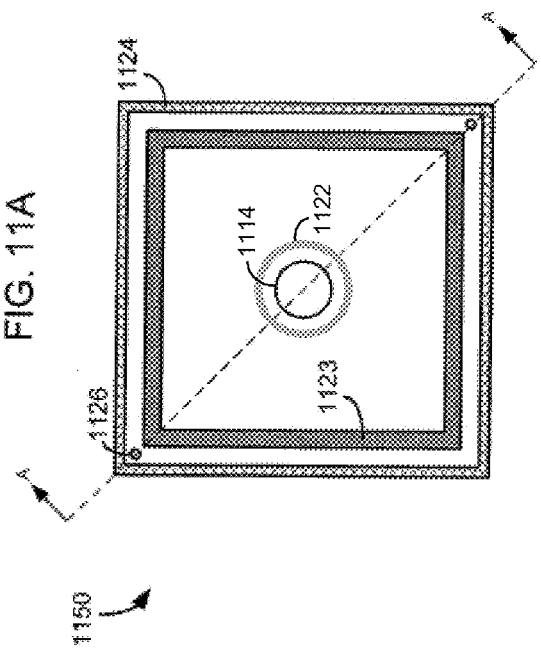
FIG. 11B is a schematic diagram of a plan view of an exemplary site of the apparatus shown in FIG. 11A, according to an embodiment of the present invention.

FIG. 11B illustrates a plan view of an exemplary site 1150 of the apparatus 1100 shown in FIG. 11A. (The sectional view shown in FIG. 11A could be taken, for example, along line A-A of FIG. 11B.) The plan view of FIG. 11B looks down on film 1104, showing opening 1114 defined by film 1104. Film 1104 is attached to the substrate 1102 underneath by adhesive 1124, which in this embodiment also provides the spacing between film 1104 and substrate 1102. Within the perimeter of adhesive 1124, site 1150 is defined by hydrophobic barrier 1123. Vents 1126 are defined by film 11104, which allow air to escape from site 1150. Although shown positioned between adhesive 1124 and barriers 1123, vents 1126 could also be positioned anywhere beyond the points to which cell suspension can reach, such as over the barriers 1123 or even proximate to adhesive 1124, assuming the adhesive does not occlude the vent. For manufacturing ease, additional hydrophobic barriers can be disposed proximate adhesive 1124 to prevent adhesive from occluding vents. In addition to the positioning of vents 1126, the number of vents 1126 could vary. Thus, although two vents 1126 are shown, any number of vents could be provided as suitable for a desired application.

Although FIGS. 11A and 11B illustrate an exemplary apparatus 1100 having an upper film and lower substrate (e.g., glass substrate), with openings and vents defined by the film, one of ordinary skill in the art would appreciate that the configuration could be reversed or otherwise altered to meet the needs of a specific implementation. For example, another exemplary apparatus could have a lower film and an upper glass or plastic cover, with the openings and vents defined by the upper cover.

FIG. 12A illustrates another embodiment of the present invention, in which cell suspension and test compound solution are deposited in separate wells connected by a passageway. As shown, an apparatus 1200 according to this embodiment includes a transparent substrate 1202, a through-hole structure 1228, and a film 1204. Substrate 1202 comprises, for example, glass or any other material that is transparent to the means for detection and has surface characteristics that enable solutions to wick or flow easily. Structure 1228 defines through holes, such as holes 1230 and 1232. Structure 1228 can be, for example, an acrylic plate. Substrate 1202 and structure 1228, which can be joined by adhesive 1224, together form wells connected by a passageway. The thickness of adhesive 1224 can define the height of the passageway. Film 1204 can be connected to structure 1228 by a pressure sensitive adhesive. Film 1204 defines an opening 1214 aligned with through-hole 1230 of structure 1228.

FIG. 12B illustrates a plan view of an exemplary site 1250 of the apparatus 1200 shown in FIG. 12A. (The sectional view shown in FIG. 12A could be taken, for example, along line A-A of FIG. 12B.) The plan view of FIG. 12B looks down on film 1204, showing opening 1214 defined by film 1204. Substrate 1202 is attached to structure 1228 by adhesive 1224, which in this embodiment also provides the spacing between substrate 1202 and structure 1228. Within the perimeter of adhesive 1224, site 1250 is defined by hydrophobic barrier 1223, a top section of which is attached to structure 1228 and a bottom section of which is attached to substrate 1202. Optionally, as shown in FIG. 12B, vents 1226 can be defined by substrate 1202 or by structure 1228, to allow air to escape from site 1250 before film 1204 is applied. Although shown positioned between adhesive 1224 and barriers 1223, vents 1226 could also be positioned anywhere beyond the points to which cell suspension can reach. For manufacturing ease, additional hydrophobic barriers can be disposed proximate adhesive 1224 to prevent adhesive from occluding vents. In addition to the positioning of vents 1226, the number of vents 1226 could vary. Thus, although two vents 1226 are shown, any number of vents could be provided as suitable for a desired application, or through-hole 1230 can function as the sole vent.

An embodiment of the present invention provides a method for performing a cell activity assay using the exemplary apparatus 1200 shown in FIG. 12A. This exemplary method is performed on apparatus 1200 with substrate 1202 and structure 1228 already assembled together. According to this method, a volume of a cell suspension (containing cells suspended in a cell suspension media) is deposited into hole 1232. This initial placement of cell suspension can be deposited all in one volume (e.g., 10 μl) or in two (or more) volumes, as is represented in FIG. 12A by the dotted line 1206*a* for the first volume deposited (e.g., 3 μl) and line 1206*b* for the second volume (e.g., 7 μl).

After the initial placement, the cell suspension flows through hole 1232, into the passageway between substrate 1202 and structure 1228, up to the hydrophobic barriers 1223, and partially up hole 1230 as is represented by line 1206*c*. The dimensions of the passageway and the interior dimensions of hole 1230 can create a wicking action that draws the cell suspension into the site, to the hydrophobic barriers 1223, and into hole 1230. In addition, to further promote the flow of the cell suspension into the space, air pushed by the cell suspension can be released through hydrophobic barriers 1223 and out of the site through a vent or vents, such as vents 1226. After cell suspension reaches hydrophobic barriers 1223, flow ceases and cell suspension assumes a static position as represented by lines 1206a, 1206b, and 1206c. The structure of the site limits the flow of the cell suspension and promotes the settling out of cells 1208 and their adherence to substrate 1202, and establishes a stationary fluid medium across which uniform diffusion can occur. At this point, apparatus 1200 can be incubated if necessary for cells 1208 to settle out of the cell suspension and adhere to substrate 1202, leaving the adhered cells 1208 surrounded by stationary cell suspension media 1206. Optionally, the cells 1208 on substrate 1202 are then read to provide a baseline reading to compare with future readings after the introduction of test compound solution 1210 into hole 1230.

Film 1204 is then placed over structure 1228 and joined to structure 1228 by adhesive, such as a pressure sensitive adhesive. Opening 1214 in film 1204 is aligned with hole 1230 of structure 1228. Film 1204 preferably, however, seals hole 1232, for example, adhering by adhesive applied around the perimeter of hole 1232. Film 1204 therefore traps air in hole 1232 and thereby further assists in limiting the flow of the cell suspension media and settled cells. In this manner, hole 1232 is pneumatically and hydraulically sealed by film 1204 (although hole 1230 is open to atmosphere), and the passageway is hydraulically sealed by hydrophobic barriers 1223, which prevents further flow of the cell suspension media.

With cell suspension media 1206 held stationary and cells 1208 settled, a test compound solution 1210 is then deposited in opening 1214 and in contact with cell suspension media 1206. Test compound solution 1210 contains the compound to be screened for cell activity. Although not shown in FIG. 12A, at this point, with the cell suspension and test compound solution 1210 deposited, a lid could be placed over film 1204 to seal the site from the external environment and limit evaporation of the solutions.

With test compound solution 1210 deposited on cell suspension media 1206, the test compound solution 1210 is in contact with cell suspension media 1206 at line 1206c. With this contact, test compound solution 1210 begins diffusing into cell suspension media 1206. The spatial stability of the solutions, as provided by the hydrophobic barriers and film 1204 sealing hole 1232, promotes an even and measurable rate of diffusion across the site. The site is then read periodically to observe the effect of the test compound solution 1210 on the cells 1208 as this diffusion progresses from hole 1230 toward hole 1232. These readings detect, for example, cell elongation and orientation, other morphological changes, temperature changes, movement of molecules and structures within a cell, and electromagnetic changes.

In an exemplary implementation of the embodiment of FIG. 12A, the single site of FIG. 12A is part of a 96-site apparatus, in which each site is approximately 9×9 mm square and the area within each site that is defined by hydrophobic barriers 1223 is approximately 7×7 mm square. Substrate 1202 can be glass or plastic, for example, and film 1204 can be Teflon™.

An alternative embodiment of the method of the present invention applies pressure differentials to the apparatus 1200 of FIG. 12A to promote diffusion as desired. For example, with the cell suspension media 1206 and test compound solution 1210 deposited and positionally static, a pressure differential can be applied to promote controlled movement between the solutions and to affect the rate of diffusion between the solutions as desired.

Figure 13:
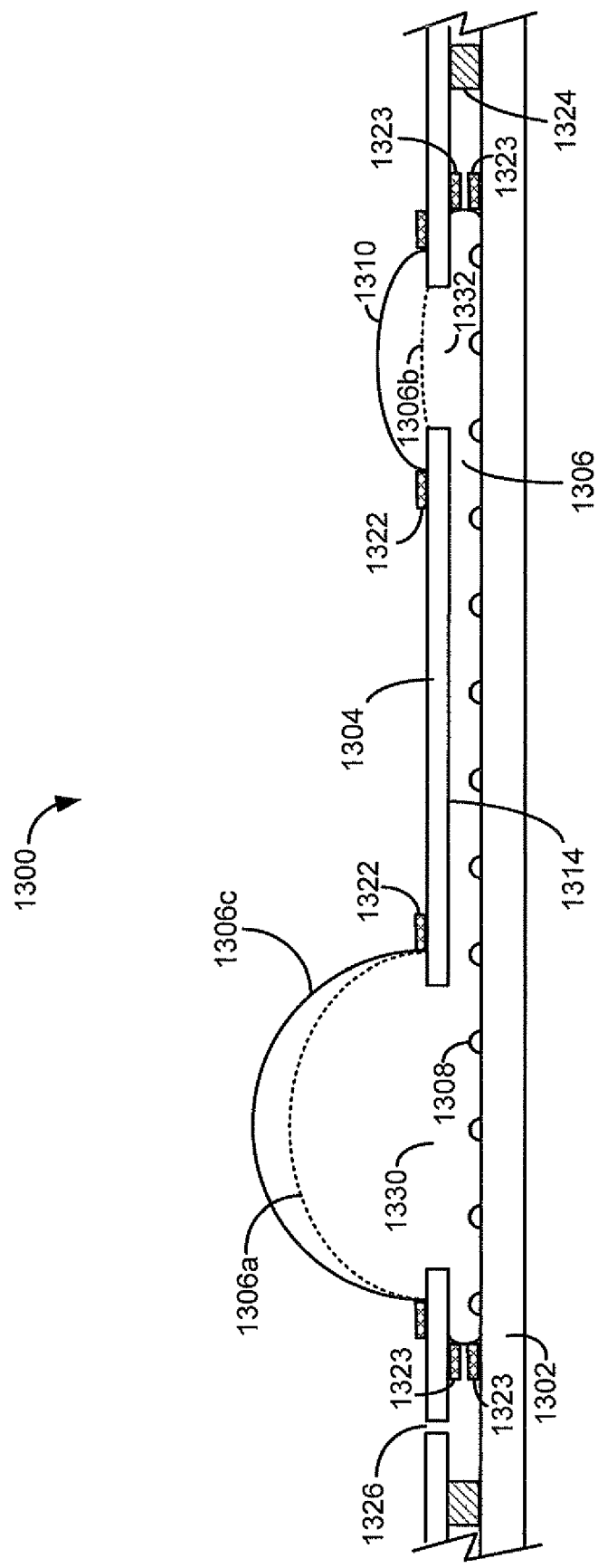
FIG. 13 is a schematic diagram of a cross-section of one site of a multi-site assay apparatus, in which cell suspension and test compound solution are deposited over separate openings in a film, with the openings connected by a passageway, according to an embodiment of the present invention.

FIG. 13 illustrates another embodiment of the present invention, in which cell suspension and test compound solution are deposited over separate openings in a film, with the openings connected by a passageway. In this embodiment, differences in volumes between the cell suspension and test compound solutions can provide the desired flow and diffusion characteristics. As shown, an apparatus 1300 according to this embodiment includes a substrate 1302 and a film 1304. Substrate 1302 comprises, for example, glass or any other material that is transparent to the means for detection and has surface characteristics that enable solutions to wick or flow easily. Film 1304 defines openings 1330 and 1332. Substrate 1302 and film 1304, which can be joined by adhesive 1324, together form a passageway that connects openings 1330 and 1332. The thickness of adhesive 1324 can define the height of the passageway. The simplicity of the construction of apparatus 1300 makes this embodiment especially suitable for denser formats, such as 1536-formats.

Apparatus 1300 can also include hydrophobic coatings to help hold cell suspension, cell suspension media, and test compound solution in place. For example, as shown in FIG. 13, the upper surface of film 1304 can have hydrophobic coatings 1322 that hold solutions in place over openings 1330 and 1332. Similarly, the bottom surface of film 1304 and the upper surface of substrate 1302 can have hydrophobic coatings 1323 that contain solutions within the site, but still allow air to pass.

An embodiment of the present invention provides a method for performing a cell activity assay using the exemplary apparatus 1300 shown in FIG. 13. This exemplary method is performed on apparatus 1300 with substrate 1302 and film 1304 already assembled as shown in FIG. 13. According to this method, a cell suspension (containing cells suspended in a cell suspension media) is deposited onto the upper surface of film 1304 over opening 1330. Hydrophobic coatings 1322 assist in holding the cell suspension in place and centering it over opening 1330. The initial placement of the cell suspension is represented in FIG. 13 by the dotted line 1306a.

After this initial placement, the cell suspension flows through opening 1330, into the space between substrate 1302 and film 1304, and up to the hydrophobic barriers 1323. The dimensions of the space can create a wicking action that draws the cell suspension into the site and to the hydrophobic barriers 1323. In addition, to further promote the flow of the cell suspension into the space, air pushed by the cell suspension can be released through hydrophobic barriers 1323 and out of the site through a vent or vents, such as vent 1326 defined by film 1304. After cell suspension reaches hydrophobic barriers 1323, flow ceases and cell suspension assumes a static position as represented by lines 1306a and 1306b. Limiting the flow of the cell suspension promotes the settling out of cells and establishes a stationary media across which uniform diffusion can occur. At this point, apparatus 1300 is incubated as necessary for cells 1308 to settle out of the cell suspension and adhere to substrate 1302, leaving the adhered cells 1308 surrounded by cell suspension media 1306. Optionally, the cells 1308 on substrate 1302 are then read to provide a baseline reading.

A test compound solution 1310 is then deposited on the upper surface of film 1304 over opening 1332. Test compound solution 1310 contains the compound to be screened for cell activity. Hydrophobic coatings 1322 assist in holding test compound solution 1310 in position over opening 1332. Although not shown in FIG. 13, at this point, with the cell suspension and test compound solution 1310 deposited, a lid could be placed over film 1304 to seal the site from the external environment and limit evaporation of the solutions, and also stabilize the solutions to limit flow. Alternatively, test compound solution 1310 can be applied to a point on the bottom surface of the lid corresponding to the hole 1330, thereby initiating diffusion of test compound solution into the cell suspension media 1306 simultaneously with sealing the site with the lid.

With test compound solution 1310 deposited on film 1304 over opening 1332, the test compound solution 1310 is in contact with cell suspension media 1306 at line 1306*b*. With this contact, test compound solution 1310 begins diffusing into cell suspension media 1306. The spatial stability of the solutions, as provided by the hydrophobic barriers, promotes an even and measurable rate of diffusion across the site. The flow and diffusion characteristics of the solutions can be further controlled as desired by regulating the relative volumes of the cell suspension media 1306 and test compound solution 1310. The forces applied by the volumes are proportional to the radius of the drops and the surface tensions of the solutions. Thus, for example, more cell suspension media can be deposited to achieve desired results (e.g., flow from cell suspension media to test compound solution), as represented by the additional cell suspension media 1306*c*. If the volumes of cell suspension media deposited at opening 1330 are greater than the volume of test compound solution 1310 deposited at opening 1332, the cell suspension media will flow from opening 1330 in the direction of opening 1332 until an equilibrium is established.

After the appropriate volumes of solutions are deposited, the site is then read periodically to observe the effect of the test compound solution 1310 on the cells 1308 as the diffusion progresses. These readings detect, for example, cell elongation and orientation, other morphological changes, temperature changes, movement of molecules and structures within a cell, and electromagnetic changes.

Instead of using the volume of the solutions to control flow and diffusion, an alternative embodiment of apparatus 1300 of FIG. 13 controls flow and diffusion using gel. A gel can limit the flow of the solutions, and control the amount of test compound solution that diffuses into the cell suspension media. According to this alternative embodiment, film 1304 could comprise a filter that is occluded except at openings 1326, 1330, and 1332. At opening 1332, filter 1304 can be unoccluded and have gel. At vent 1326 and opening 1330, filter can be unoccluded and define a clear opening without gel (e.g., a hole punched in filter 1304).

The gel at opening 1332 limits flow between test compound solution 1310 and cell suspension media 1306, and controls the diffusion of the test compound solution 1310 into cell suspension media 1306. In this manner, the relative volumes of the solutions do not affect flow or diffusion. Cell suspension media can be deposited in a single volume through opening 1330 and can flow to hydrophobic barriers 1324 and the gel disposed at opening 1332. After cells 1308 settle out of the cell suspension media, the test compound solution 1310 can be deposited at opening 1332 without regard to the relative volumes of the solutions. This alternative embodiment can therefore compensate for inaccuracies in pipetting.

Although the embodiments described above involve cell suspensions that are incubated to allow cells to settle and adhere to a film, an alternative embodiment of the present invention accommodates assays of cells that do not adhere to a film and instead stay suspended in the cell suspension. These non-adherent cells could include, for example, sperm or bacteria. In these cases, the effect of the diffusion gradient can still be observed. In other words, even if the cells are moving, a researcher can observe the progressive ring effect as the test compound solution diffuses farther from the point source and reaches and activates additional cells.

According to another embodiment of the present invention, a test compound from a compound library is applied in liquid form to a particle or bead. The liquid test compound is then gelled or dried on the particle or bead. The particle or bead is then submersed in a cell suspension media having cells (either settled and adhered to a surface, or non-adherent), after which diffusion into the cell suspension media occurs and the effect on the cells is periodically read. The particle or bead is preferably coded (e.g., color coded beads having bands of color) to indicate what testing compound solution has been applied to the particle or bead.

The particles or beads can be coated with media (water) soluble coating. The particles or beads could be small vessels, e.g., pieces of capillary tubing or hollow balls having a small hole in their surface. In the case of hollow balls, the balls could be filled by applying a vacuum while the balls are in a test compound solution. When the vacuum is released, the solution fills the balls.

The particles or beads could also be sintered material, e.g., metal, plastic, glass, or ceramic particles coded by color, shape, or some combination thereof. These particles would be filled with test compound solution using a vacuum in a manner similar to the hollow balls.

The particles or beads could also be pieces of cellulose filter with a skin applied on the top and bottom. According to this implementation, a skin is applied to the top and bottom sides of a sheet of filter with, for example, a silkscreen. Small holes are formed in the skin on the top side of the filter sheet. A drop of test compound solution is applied over each hole. A vacuum is applied and released (several times, if necessary) to draw the test compound solution into the filter sheet between the top and bottom skins. If necessary, excess test compound solution is removed from the top of the top skin. A drop of cell suspension is then deposited over each of the holes in the top skin. The drops of cell suspension are then covered with a film. Optionally, the cell suspension could be applied first to the film (allowing the cells to settle, if desired) and the film inverted over the top skin of the filter, which holds the test compound solution.

The present invention is adaptable to a variety of assay formats. In one example, the present invention could be applied to assay apparatus complying with the Society for Biomolecular Screening (SBS) microplate format. Such apparatus could include individual microplates having 96, 384, or 1536 sites, which are typically used in automated systems that assay a high volume of compounds. The various embodiments of the individual site constructions described above would be replicated across the multiple sites of the SBS plate. As one of ordinary skill in the art would appreciate, however, the use of these individual site constructions is not limited to the SBS format, and could indeed be applied to other standard and non-standard formats.

As an example of an alternative format, the present invention could be applied to assay apparatus that use continuous films. The films could be conveyed on reels, for example, with the aid of sprockets in the reels and corresponding sprocket holes in the films. The reels would convey the films from one station to the next, where each step of the methods described above would occur.

For example, with reference to the embodiment of FIG. 1, a first station could be a liquid dispensing station that deposits cell suspension onto the first side of film 102 over a group (e.g., a row) of openings in the film 102, such as the opening 110 shown in FIG. 1. That group of sites would then be conveyed along with the film to an incubation station, where the cells 108 would settle and adhere to the film 102. After incubation, the group of sites would move on to a first detector that provides a baseline reading of the cells 108. The group of sites would then move to a second liquid dispensing station that deposits the test compound solution 106 on the second side of the film 102, e.g., using an inverted pin applicator system. The group of sites would then be conveyed to one or more incubation stations and/or one or more detectors, as necessary to complete the assay.

The continuous film embodiment can include multiple films and support structures. The films or films with support structures (e.g., thicker films) are laminated together during the assay process sandwiching the cells and test compounds, thereby eliminating evaporative effects.

Using a continuous film in conjunction with the present invention provides an inexpensive and efficient assay method. The film is also convenient to convey, providing a simple and accurate means of automation. The continuous film also enables multiple, successive detection steps, as the test sites progress from start to finish in an assembly line fashion.

As another example of an alternative format, the present invention could be applied to assay apparatus that use a revolving, multiple-site platform, such as a compact disc. In this case, the groups of sites could be in rows extending radially from the center of the platform. The platform would rotate to take each group of sites through the various stations. This format can provide an extremely flat, optically favorable surface through which cell changes can be detected.

The present invention provides many benefits, including but not limited to one or more of the following:

1) uses few cells;
2) uses small amounts of test compound;
3) completes assays up to 10-1000 times faster than conventional cell migration assays;
4) lowers costs by enabling high density studies (i.e., low cost per test per compound);
5) lowers coefficients of variation, including preventing coefficients of variation due to pipetting errors from passing through to the coefficients of variation of the assay, and consequently, enables cell based HCS and HTS;
6) obtains kinetic data as well as quantitative data, as opposed to, for example, migration assays that count the number or percentage of cells that have passed through a filter, but yield no data about the cells that have not passed through the filter;
7) reduces reagent costs by virtue of the low number of cells and low volume of compounds needed;
8) provides optically advantageous assay apparatus that enables relatively distortion free viewing by high resolution optical detection systems;
9) enables the use of primary cells, i.e., cells directly from patients, as opposed to immortal cell lines;
10) is geometrically compatible with a high resolution optical detection systems, which require flat, transparent tops and bottoms and relatively thin layers (between 0.1-2.0 mm thick); and
11) helps avoid evaporation problems by sandwiching the cell suspension and test compounds in a sealed environment.

The present invention allows researchers to gather cell data related to, for example, cell orientation, shape, and morphology. In complicated assays such as angiogenesis, the present invention obtains data on whether angiogenesis is observed taking place or is not. In addition, more data can be gathered by, for example, adding different compounds to the cells undergoing angiogenesis to determine if the angiogenesis can be reversed or inhibited.

Obtaining kinetic data can also significantly lower the coefficient of variation of a study. With traditional cell activity assays, large variations in test sites as well as positive and negative control sites result in unacceptably high coefficients of variation. Indeed, researchers usually use duplicate or triplicate sites for each test compound and repeat traditional cell activity assays two and three times to confirm results. In contrast, the present invention enables kinetic studies that significantly lower the coefficient of variation. These kinetic studies identify changes in the cells and cell populations progressively. A researcher (or detection system) can observe a pattern of cell activity progress geometrically through a population of cells as diffusion of a test compound moves through that population, or observe no progressive pattern. Changes in cell activity progressing geometrically (in a concentric pattern) in lock step with the diffusion of a test compound in that same concentric pattern are qualitatively different from assays that cannot use kinetic patterns. Detecting these patterns establishes a causal relationship. Therefore, this approach virtually eliminates false positives and the irregularities common with current cell based assays.

A researcher using the present invention can also determine when cells that are responsive to the test compound solution are affecting adjacent cells. For example, by monitoring the diffusion rate of the test compound solution, a researcher can determine when cells should respond based on their distance from the point source. If these cells show changes before that time, then the researcher can deduce that the cells that are already responding are being affected by adjacent cells before the test compound solution reaches those cells. Such information could be especially valuable for secondary and tertiary screens.

Although the figures and description refer to point source diffusion, it should be evident that there can be more than one point source in a site of an apparatus. What is relevant with respect to the number of the point sources is that they are far enough apart for the kinetics of the phenomena being studied to be clear. For example, if there is a pattern of point sources in an assay site, they must be far enough apart not to interfere with one another during the course of the assay. Furthermore, several point sources can be used, one with a known inhibitor of a cellular activity and another with a compound from the library. As the diffusion front of the inhibitor intersects with the test compound diffusion front, the pattern of cell activity will show a characteristic pattern.

In describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, claims directed to the method and/or process of the present invention should not be limited to the performance of their steps in the order written, unless that order is explicitly described as required by the description of the process in the specification. Otherwise, one skilled in the art can readily appreciate that the sequences may be varied and still remain within the spirit and scope of the present invention.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims, and by their equivalents.

What is claimed is:

1. An apparatus for exposing cells to a test compound solution diffused from a point source to determine whether the test compound solution induces progressive cell activity response in the cells, the apparatus comprising:
   a substrate;
   a cover applied over the substrate such that a passageway is defined between the cover and the substrate, wherein the cover has an outer perimeter, wherein the cover defines an opening inside the outer perimeter, and wherein the opening is in fluid communication with the passageway; and
   a hydrophobic barrier disposed within the passageway,
   wherein the hydrophobic barrier defines a test site perimeter of a test site,
   wherein the test site perimeter is disposed within the outer perimeter of the cover when the cover is viewed from a plan view perpendicular to a plane defined by the cover,
   wherein the opening is disposed within the test site perimeter when the cover is viewed from the plan view,
   wherein the substrate, the cover, and the hydrophobic barrier are configured to contain the cells within the test site,
   wherein the hydrophobic barrier limits passage of liquid outside of the test site and allows passage of gas outside of the test site, and
   wherein the opening is the only opening defined by the cover within the test site perimeter.

2. The apparatus of claim 1, wherein the cover defines a vent disposed outside of the test site.

3. The apparatus of claim 1, further comprising an adhesive joining the cover and the substrate and defining a distance at which the cover and the substrate are held apart, thereby defining a dimension of the passageway, wherein the adhesive is disposed outside the hydrophobic barrier.

4. The apparatus of claim 3, wherein the adhesive comprises a physical barrier that surrounds the hydrophobic barrier and does not allow the passage of liquid or gas.

5. The apparatus of claim 4, wherein the physical barrier is shaped as a square around the hydrophobic barrier.

6. The apparatus of claim 1, wherein the substrate is transparent.

7. The apparatus of claim 6, wherein the substrate comprises glass.

8. The apparatus of claim 1, wherein the substrate allows passage of electromagnetic radiation.

9. The apparatus of claim 1, wherein the cover comprises one of film and glass.

10. An apparatus for exposing cells to a test compound solution diffused from a point source to determine whether the test compound solution induces progressive cell activity response in the cells, the apparatus comprising:
    a substrate;
    a cover applied over the substrate such that a passageway is defined between the cover and the substrate, wherein the cover defines an opening in fluid communication with the passageway; and
    a hydrophobic barrier disposed within the passageway,
    wherein the hydrophobic barrier defines a test site,
    wherein the substrate, the cover, and the hydrophobic barrier are configured to contain the cells within the test site,
    wherein the hydrophobic barrier limits passage of liquid outside of the test site and allows passage of gas outside of the test site, and
    wherein the hydrophobic barrier comprises:
       a first barrier portion applied to a side of the substrate facing the cover, wherein the first barrier portion is continuous so as to enclose an area on the substrate, wherein the area comprises the test site, and
       a second barrier portion applied to a side of the cover facing the substrate, wherein the second barrier portion is continuous and is disposed generally opposite to the first barrier portion, and wherein the first barrier portion and the second barrier portion are separated by a gap that allows the passage of gas outside of the test site.

11. The apparatus of claim 1, wherein the opening defined by the cover is aligned substantially with a geometric center of a shape of the test site perimeter when viewed from the plan view.

12. The apparatus of claim 1, wherein the cover further comprises a hydrophobic coating on a side of the cover opposite to the substrate, and wherein the hydrophobic coating is configured to hold a cell suspension in place over the opening defined by the cover.

13. The apparatus of claim 12, wherein the hydrophobic coating is configured to hold the cell suspension centered over the opening defined by the cover.

14. The apparatus of claim 12, wherein the cover comprises a glass cover.

15. The apparatus of claim 12, wherein the cover comprises a plastic cover.

16. The apparatus of claim 1, wherein the substrate and the cover define a plurality of test sites configured substantially the same as the test site.

17. The apparatus of claim 1, wherein the cover and the substrate are separated by a distance ranging from approximately 10µ to approximately 200µ.

18. The apparatus of claim 1, wherein the test site defined by the substrate, the cover, and the hydrophobic barrier has a volume ranging from approximately 1 µl to 5 µl.

19. The apparatus of claim 1, wherein the opening is a substantially circular opening that narrows in a direction from a side of the cover opposite to the substrate to a side of the cover facing the substrate.

20. The apparatus of claim 1, further comprising a lattice plate joining the cover and the substrate and defining a distance at which the cover and the substrate are held apart, thereby defining a dimension of the passageway, wherein the lattice plate defines a through-hole in which is disposed the test site defined by the hydrophobic barrier.

21. The apparatus of claim 1, wherein the hydrophobic barrier supports the cover and the substrate, separates the cover and the substrate from each other, and defines a distance at which the cover and the substrate are held apart, thereby defining a dimension of the passageway.

22. An apparatus for exposing cells to a test compound solution diffused from a point source to determine whether the test compound solution induces progressive cell activity response in the cells, the apparatus comprising:
    a transparent substrate;
    an adhesive layer;
    a cover adhered to the substrate by the adhesive layer such that a passageway is defined between the cover and the substrate, wherein the cover has an outer perimeter, wherein the cover defines an opening inside the outer perimeter, wherein the opening is in fluid communication with the passageway, and wherein the adhesive layer defines a distance at which the cover and the substrate are held apart, thereby defining a dimension of the passageway; and a hydrophobic barrier disposed within the passageway, wherein the hydrophobic barrier defines a test site perimeter of a test site, wherein the test site perimeter is disposed within the outer perimeter of the cover when the cover is viewed from a plan view perpendicular to a plane defined by the cover, wherein the opening is disposed within the test site perimeter when the cover is viewed from the plan view, wherein the substrate, the cover, and the hydrophobic barrier are configured to contain the cells within the test site, wherein the hydrophobic barrier limits passage of liquid outside of the test site and allows passage of gas outside of the test site, wherein the adhesive layer comprises a physical barrier that surrounds the hydrophobic barrier and does not allow the passage of liquid or gas, and wherein the cover defines a vent disposed between the hydrophobic barrier and the adhesive layer when viewed from the plan view, wherein the vent allows passage of gas to outside of the apparatus.

23. The apparatus of claim 22, wherein the opening is the only opening defined by the cover within the test site perimeter.

24. The apparatus of claim 1, wherein the hydrophobic barrier is applied to at least one of a side of the substrate facing the cover and a side of the cover facing the substrate, and wherein the hydrophobic barrier defines a gap that allows the passage of gas outside of the test site.

25. The apparatus of claim 22, wherein the opening defined by the cover is aligned substantially with a geometric center of a shape of the test site perimeter when viewed from the plan view.

* * * * *